(12) United States Patent
Sonderegger et al.

(10) Patent No.: US 11,628,290 B2
(45) Date of Patent: *Apr. 18, 2023

(54) PINCH CLAMP

(71) Applicant: Becton, Dickinson and Company, Franklin Lakes, NJ (US)

(72) Inventors: Ralph L. Sonderegger, Farmington, UT (US); Jonathan Karl Burkholz, Salt Lake City, UT (US); Weston F. Harding, Lehi, UT (US); Olivia Hu, Shanghai (CN); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 103 days.

This patent is subject to a terminal disclaimer.

(21) Appl. No.: 16/774,980

(22) Filed: Jan. 28, 2020

(65) Prior Publication Data

US 2020/0164200 A1 May 28, 2020

Related U.S. Application Data

(62) Division of application No. 15/286,308, filed on Oct. 5, 2016, now Pat. No. 10,589,082.

(Continued)

(51) Int. Cl.
    *A61M 39/28* (2006.01)
(52) U.S. Cl.
    CPC .......... *A61M 39/28* (2013.01); *A61M 39/284* (2013.01); *A61M 2207/00* (2013.01)
(58) Field of Classification Search
    CPC ..... A61M 39/28; A61M 39/284; F16K 7/063; G05G 1/08; G05G 1/10
    See application file for complete search history.

(56) References Cited

U.S. PATENT DOCUMENTS 3,344,966 A  10/1967  Schaefer
3,698,681 A  10/1972  Lacey
(Continued)

FOREIGN PATENT DOCUMENTS

AU   2016346886    5/2017
CN   101569768 A   11/2009
(Continued)

OTHER PUBLICATIONS

"Coating", Macmillan Dictionary, www.macmillandictionary.com/us/dictionary/american/coating. Accessed Mar. 5, 2019.

*Primary Examiner* — Laura A Bouchelle
(74) *Attorney, Agent, or Firm* — Kirton McConkie; Whitney Blair; Kevin Stinger

(57) ABSTRACT

A pinch clamp for use in occluding intravenous tubing or other similar tubing can include patient comfort features and/or lateral disengagement prevention features. These features can also be designed in a manner that allows the pinch clamps to be more easily manufactured. A pinch clamp can include a first arm that is coupled to a second arm by hinges. Each of the first and second arms can form a clamping surface that are aligned when the first arm is positioned overtop the second arm. The first arm can include opposing openings and the second arm can include opposing tabs which insert through the openings when the first arm is positioned overtop the second arm. The retaining tabs interface with the openings to prevent the first arm from separating from the second arm.

15 Claims, 22 Drawing Sheets

Related U.S. Application Data

(60) Provisional application No. 62/296,390, filed on Feb. 17, 2016.

(56) References Cited

U.S. PATENT DOCUMENTS

| | | | |
|---|---|---|---|
| 3,924,307 A | 12/1975 | Tate | |
| 4,053,135 A | 10/1977 | Salfaris | |
| 4,115,182 A | 9/1978 | Wildmoser | |
| 4,235,412 A * | 11/1980 | Rath | A61M 39/284 251/10 |
| 4,346,869 A * | 8/1982 | MacNeill | A61M 39/284 251/10 |
| 4,676,476 A * | 6/1987 | Herrli | A61M 39/284 251/9 |
| 4,854,766 A | 4/1989 | Hein | |
| 4,892,276 A | 1/1990 | Alessio | |
| 5,292,312 A | 3/1994 | Delk et al. | |
| 5,318,546 A | 6/1994 | Bierman | |
| 5,398,679 A | 3/1995 | Freed | |
| 5,842,932 A | 12/1998 | Goddard | |
| 5,865,813 A | 2/1999 | DeKalb et al. | |
| 5,989,174 A | 11/1999 | Patrizio | |
| 6,079,328 A | 6/2000 | Beck | |
| 6,095,479 A | 8/2000 | Brindisi | |
| 6,162,201 A | 12/2000 | Cohen et al. | |
| 6,279,256 B1 | 8/2001 | Norolof et al. | |
| 6,349,727 B1 | 2/2002 | Stewart, Jr. et al. | |
| D465,843 S | 11/2002 | Guala | |
| 6,942,647 B2 | 9/2005 | Nickels | |
| 7,300,172 B1 | 11/2007 | Lefler | |
| 7,350,761 B1 | 4/2008 | Stuart | |
| 7,686,279 B2 * | 3/2010 | Nerbonne | A61M 39/284 604/250 |
| 8,262,639 B2 * | 9/2012 | Mathias | F16K 7/063 604/403 |
| 8,267,370 B2 | 9/2012 | Fisher et al. | |
| 8,636,260 B2 | 1/2014 | Gauger et al. | |
| 10,082,241 B2 | 9/2018 | Janway et al. | |
| 10,173,018 B1 * | 1/2019 | Rucker | A61M 25/02 |
| 10,280,955 B2 | 5/2019 | Mohika et al. | |
| 10,589,082 B2 * | 3/2020 | Sonderegger | A61M 39/284 |
| 2002/0161333 A1 | 10/2002 | Luther | |
| 2003/0074009 A1 | 4/2003 | Ramsey et al. | |
| 2004/0089828 A1 * | 5/2004 | Werth | A61M 39/284 251/10 |
| 2004/0092887 A1 | 5/2004 | Nickels | |
| 2005/0125013 A1 | 6/2005 | Kessler | |
| 2005/0215975 A1 | 9/2005 | Mathias et al. | |
| 2006/0081797 A1 | 4/2006 | Zerfas | |
| 2010/0152681 A1 | 6/2010 | Mathias | |
| 2010/0232497 A1 | 9/2010 | MacInnis et al. | |
| 2010/0252702 A1 | 10/2010 | Spang, Jr. et al. | |
| 2012/0004624 A1 | 1/2012 | Brown et al. | |
| 2012/0035553 A1 | 2/2012 | Lombardo et al. | |
| 2012/0083803 A1 | 4/2012 | Patel et al. | |
| 2012/0232497 A1 * | 9/2012 | Singh | A61M 39/284 604/250 |
| 2012/0316539 A1 | 12/2012 | Villasana | |
| 2013/0066280 A1 | 3/2013 | Wallin | |
| 2013/0131608 A1 | 5/2013 | Davis et al. | |
| 2013/0272773 A1 | 10/2013 | Kamen et al. | |
| 2013/0310768 A1 | 11/2013 | Ebara et al. | |
| 2013/0324975 A1 | 12/2013 | Douglas et al. | |
| 2014/0060655 A1 | 3/2014 | Ramos et al. | |
| 2014/0227021 A1 | 8/2014 | Kamen et al. | |
| 2014/0259548 A1 | 9/2014 | Perullo | |
| 2016/0355205 A1 | 12/2016 | Upton et al. | |
| 2017/0007257 A1 | 1/2017 | Potter et al. | |
| 2017/0082207 A1 | 3/2017 | Tran | |
| 2017/0246444 A1 | 8/2017 | Domatch et al. | |
| 2018/0245699 A1 | 8/2018 | Lee | |
| 2020/0246012 A1 | 8/2020 | Shelton, IV et al. | |

FOREIGN PATENT DOCUMENTS

| | | |
|---|---|---|
| DE | 102005004863 | 8/2006 |
| EP | 1555007 | 7/2005 |
| EP | 2332611 | 6/2011 |
| EP | 2589395 | 5/2013 |
| FR | 2590645 | 5/1987 |
| JP | S52-052394 | 4/1977 |
| JP | S55-097593 | 7/1980 |
| JP | H02 4384 | 1/1990 |
| JP | H04-193179 | 7/1992 |
| JP | H05329210 | 12/1993 |
| JP | 2000088120 | 3/2000 |
| JP | 2001259030 | 9/2001 |
| JP | 2003245349 | 9/2003 |
| JP | 2006141988 | 6/2006 |
| JP | 2009532137 | 9/2009 |
| JP | 2013176543 | 9/2013 |
| WO | 99/18377 | 4/1999 |
| WO | 2007/112500 | 10/2007 |
| WO | 2007/133291 | 11/2007 |
| WO | 2008/024440 | 2/2008 |
| WO | 2010/109279 | 9/2010 |
| WO | 2011/035367 | 3/2011 |
| WO | 2017/074681 | 5/2017 |

\* cited by examiner

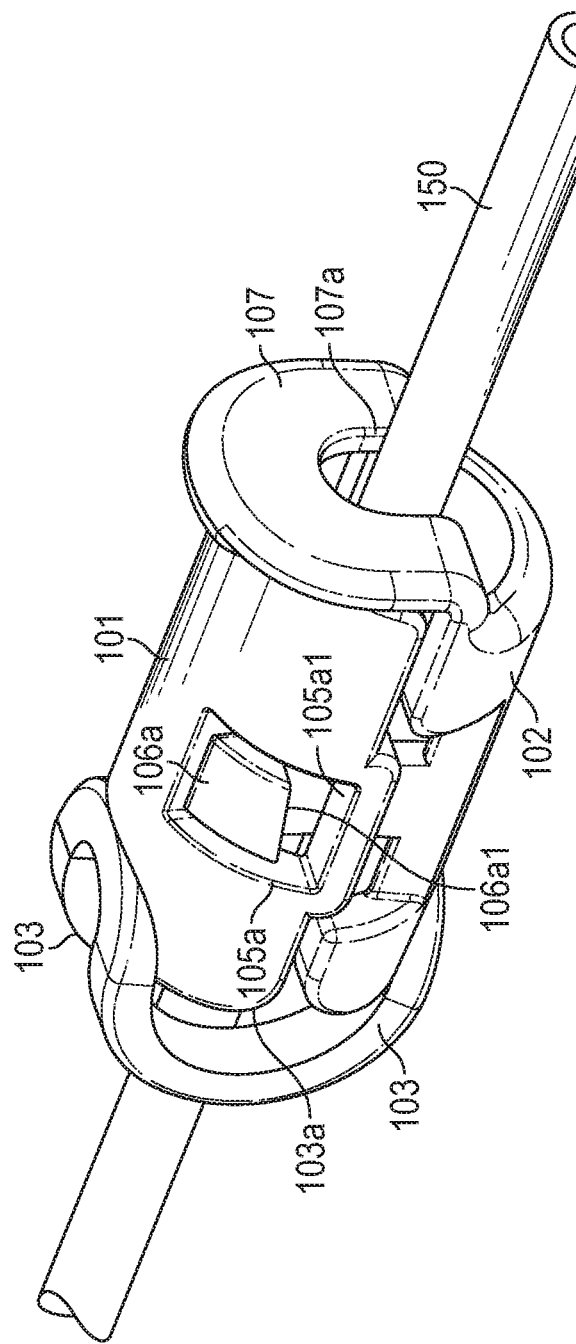
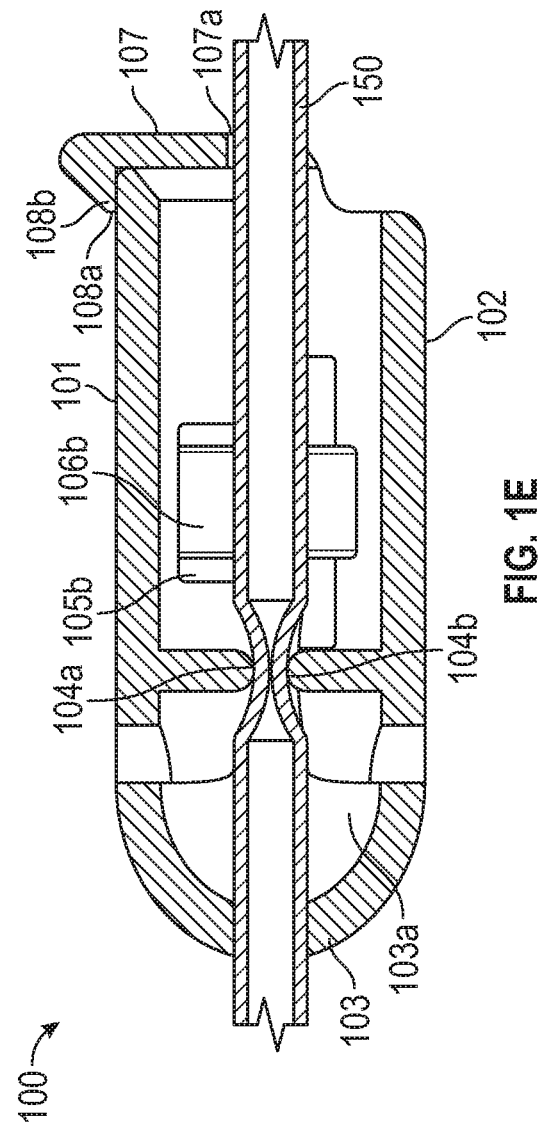
FIG. 1D
FIG. 1E

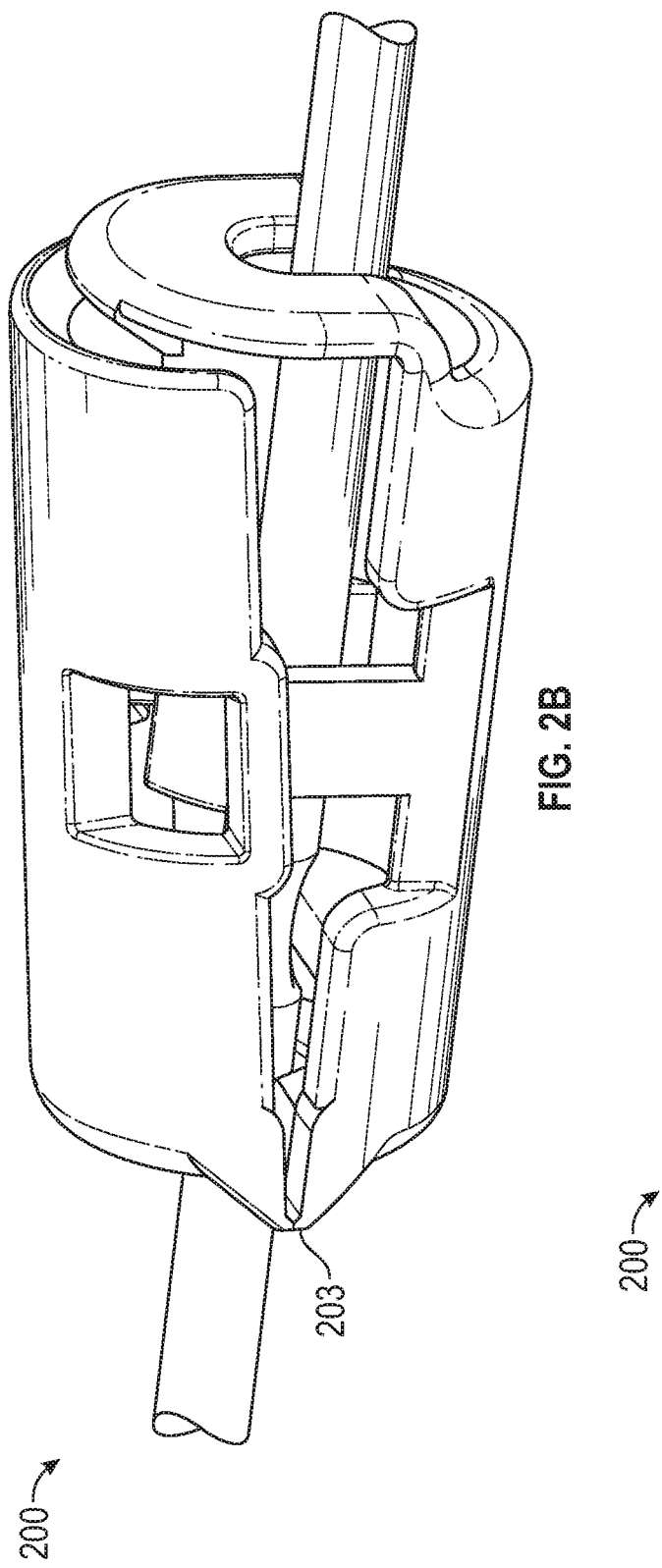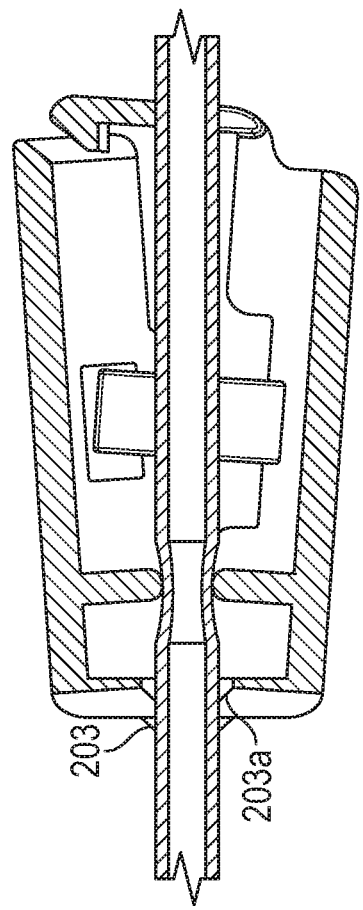
FIG. 2B
FIG. 2C

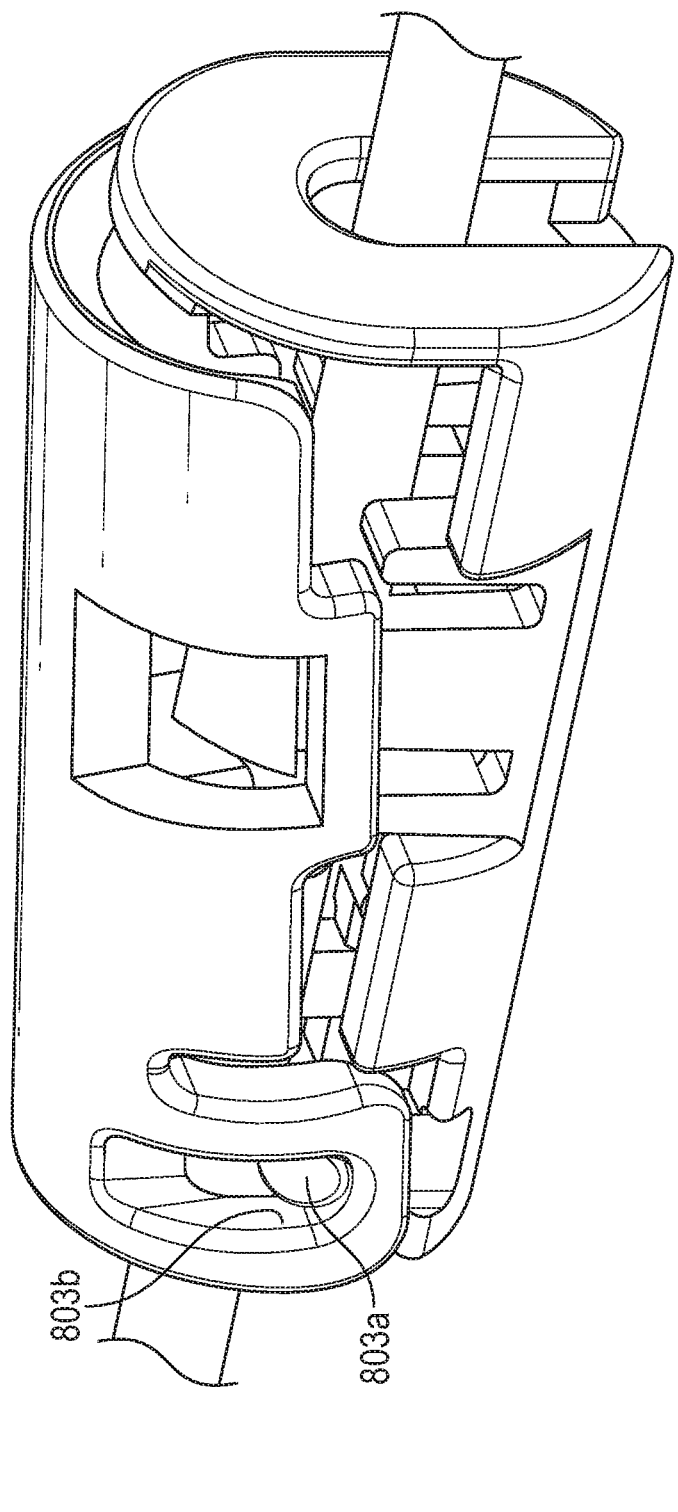

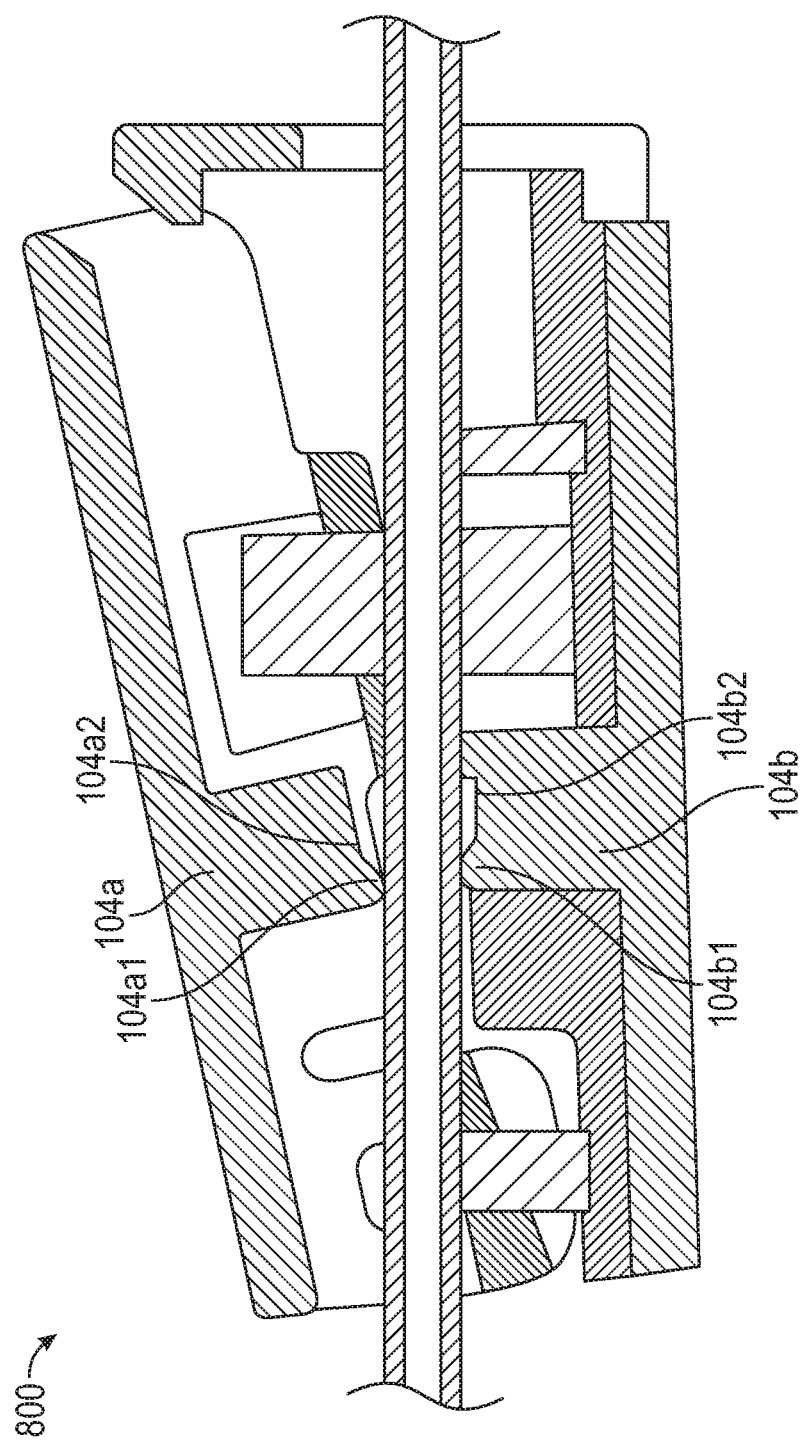

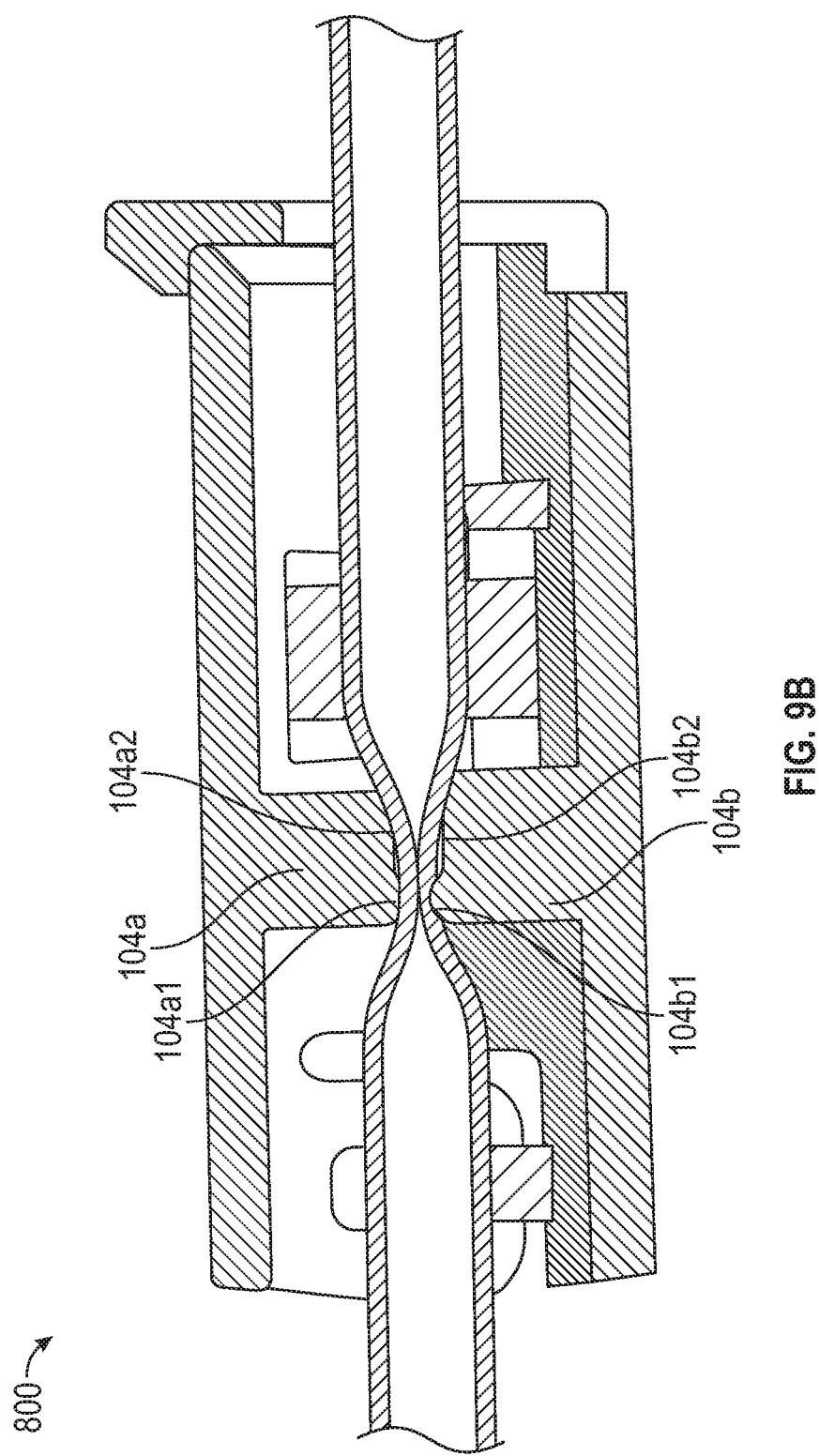

PINCH CLAMP

RELATED APPLICATIONS

This application is a divisional of U.S. patent application Ser. No. 15/286,308, filed Oct. 5, 2016, entitled PINCH CLAMP, which claims the benefit of U.S. Provisional Patent Application No. 62/296,390 which was filed on Feb. 17, 2016 and is incorporated herein by reference in their entirety.

BACKGROUND OF THE INVENTION

The pinch clamp is a well-known type of one-piece plastic clamp which is used to close off intravenous tubing. The pinch clamp generally comprises a smooth, hard plastic material that is resilient and capable of controlled flexion to enable engagement and disengagement of the clamping surfaces.

The molding or extrusion process of manufacturing a pinch clamp generally results in the clamp having sharp edges which may scratch or otherwise irritate the patient with which the clamp is used. Further, the hard, smooth properties of the clamp's plastic create difficulty in grasping and manipulating the clamp during use, especially when the clamp becomes wet. In some instances, the hard, smooth properties of the clamp's plastic further results in unintentional disengagement of the clamp when a lateral force (i.e., a force in a direction perpendicular to the length of tubing) is applied to the interlocked arms of the clamp.

Thus, although methods and devices currently exist for clamping a section of tubing using a pinch clamp, challenges still remain. Accordingly, the features of the present invention address and overcome these challenges.

BRIEF SUMMARY OF THE INVENTION

The present invention is directed to pinch clamps that are designed for use in clamping or occluding intravenous tubing. More particularly, a pinch clamp in accordance with embodiments of the present invention can include patient comfort features and/or lateral disengagement prevention features. These features can also be designed in a manner that allows the pinch clamps to be more easily manufactured and assembled.

In one embodiment, the present invention is implemented as a pinch clamp that includes a first arm that is coupled to a second arm by hinges. Each of the first and second arms can form a clamping surface that are aligned when the first arm is positioned overtop the second arm. The first arm can include opposing openings and the second arm can include opposing retaining tabs which insert through the openings when the first arm is positioned overtop the second arm. The retaining tabs interface with the openings to prevent the first arm from separating from the second arm.

In another embodiment, the present invention can be implemented as a pinch clamp that includes a first arm having a rounded shape that includes opposing openings. The first arm forms a first clamping surface. The pinch clamp can also include a second arm having a rounded shape that includes opposing retaining tabs. The second arm can also form a second clamping surface. The pinch clamp can further include opposing hinges that couple the first arm to the second arm such that, when the first arm is positioned overtop the second arm, the retaining tabs insert into the openings and secure the first arm to the second arm.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1D illustrates the pinch clamp of FIG. 1A in an assembled, engaged position;

FIG. 1E illustrates a cross-sectional side view of the pinch clamp of FIG. 1A in the assembled, engaged position;

FIG. 2B illustrates the pinch clamp of FIG. 2A in an assembled, disengaged position;

FIG. 2C illustrates a cross-sectional side view of the pinch clamp of FIG. 2A in the assembled, disengaged position;

FIGS. 8A-8C illustrate a pinch clamp in accordance with one or more additional embodiments of the present invention in which the pinch clamp includes a separable hinge that allows the arms of the pinch clamp to be assembled in a linear fashion.

FIGS. 9A and 9B illustrate how a pinch clamp in accordance with one or more embodiments of the present invention can include clamping surfaces that provide positive displacement of a fluid contained within the intravenous tubing.

DETAILED DESCRIPTION OF THE INVENTION

Figure 1A:
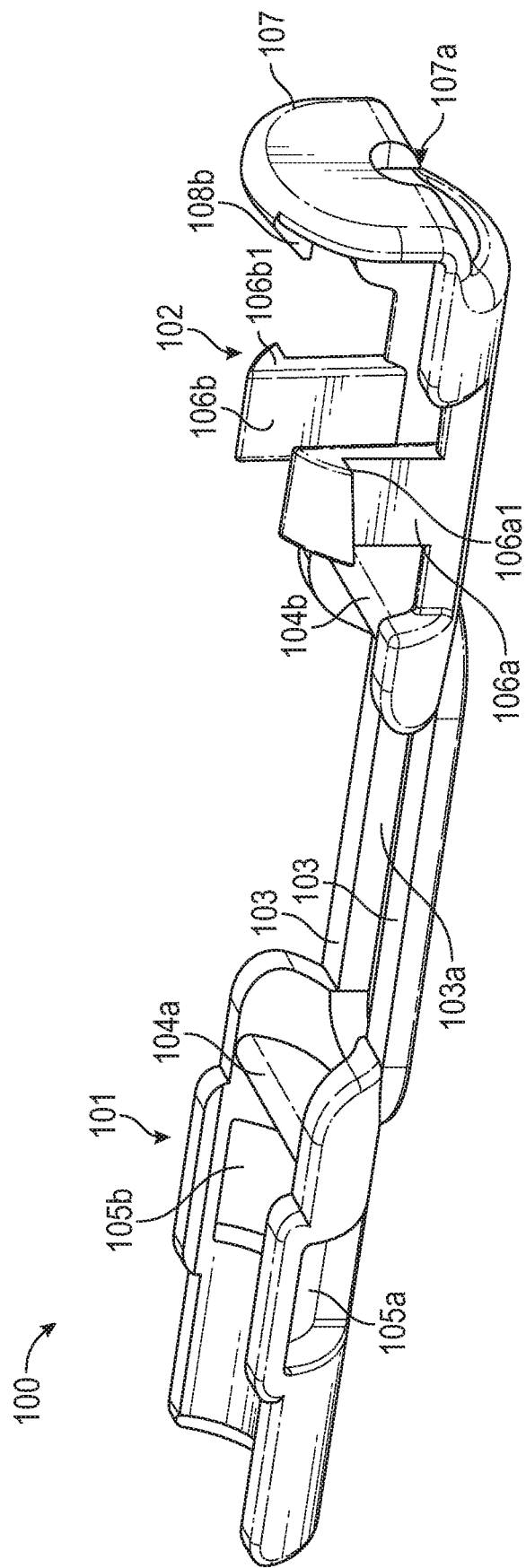
FIG. 1A illustrates a pinch clamp in accordance with one or more embodiments of the present invention in which the pinch clamp is oriented in a pre-assembled position.
Figure 1B:
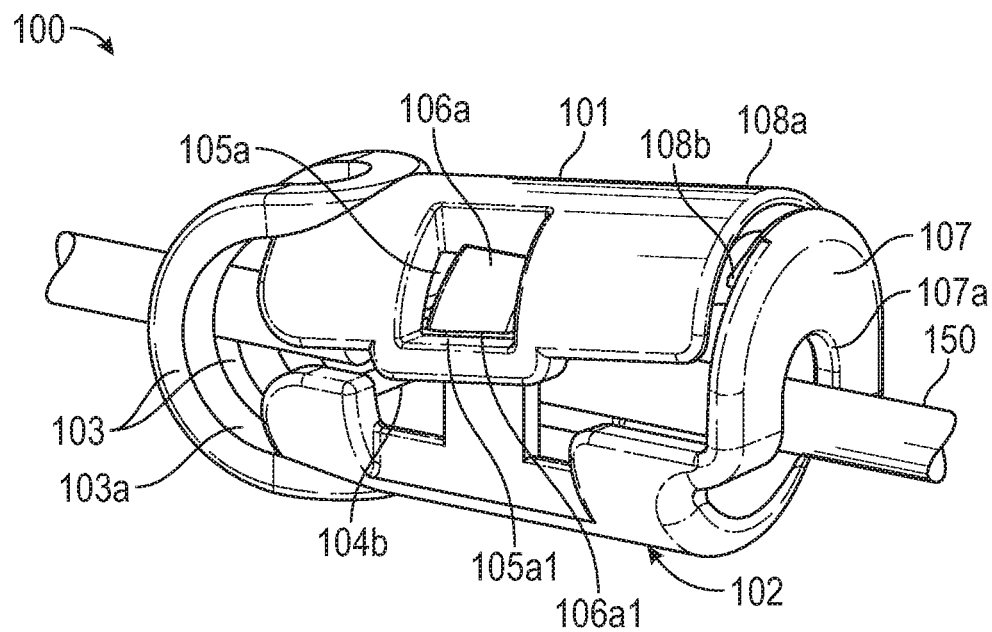
FIG. 1B illustrates the pinch clamp of FIG. 1A in an assembled, disengaged position.
Figure 1C:
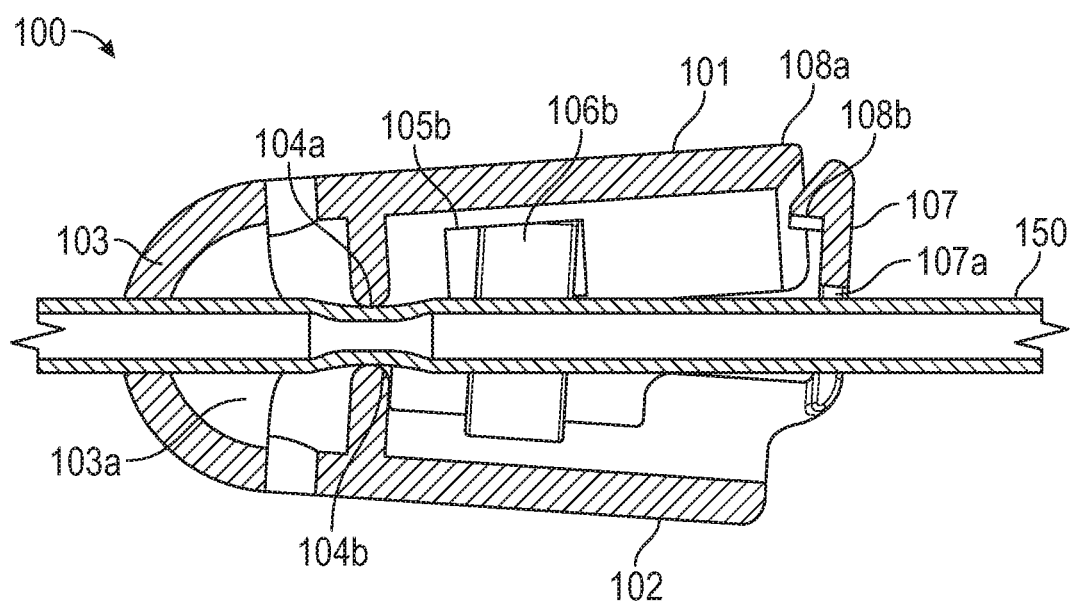
FIG. 1C illustrates a cross-sectional side view of the pinch clamp of FIG. 1A in the assembled, disengaged position.
Figure 2A:
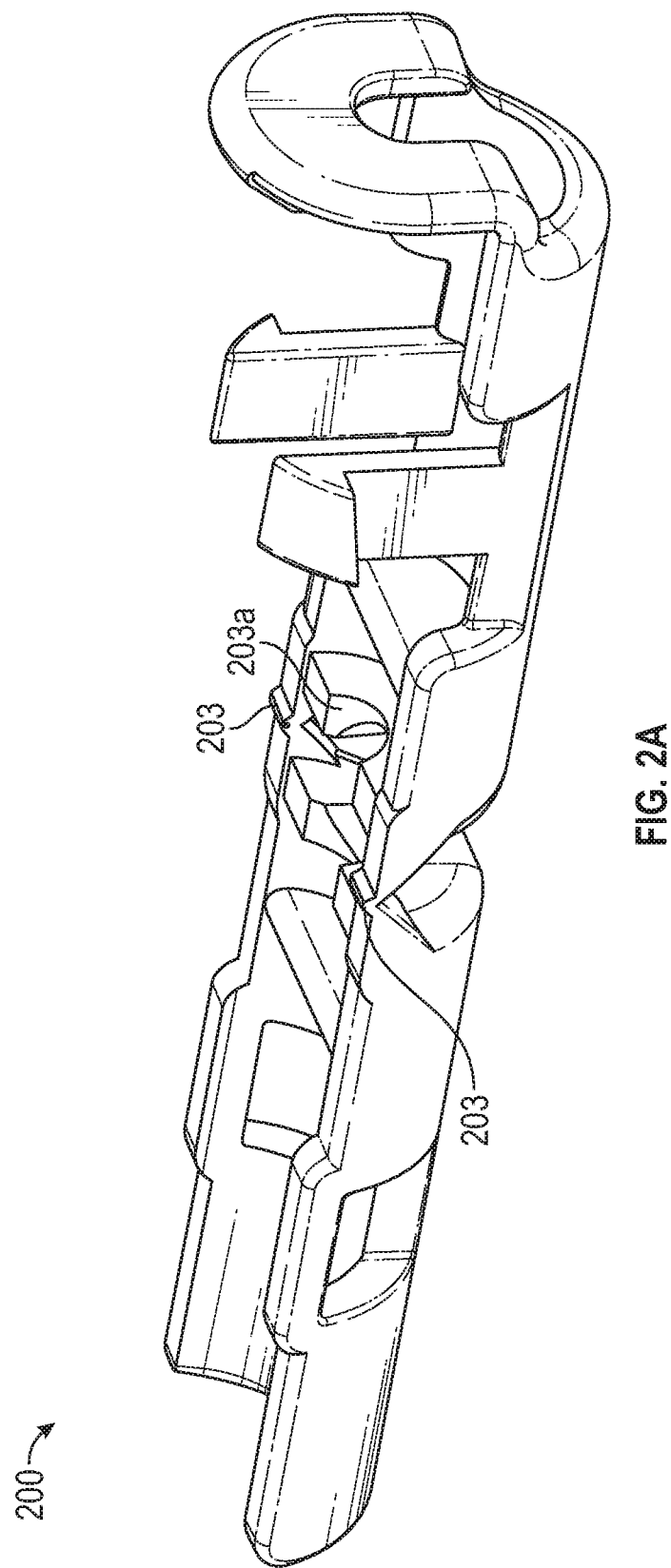
FIG. 2A illustrates a pinch clamp in accordance with one or more additional embodiments of the present invention in which the pinch clamp is oriented in a pre-assembled position.
Figure 2D:
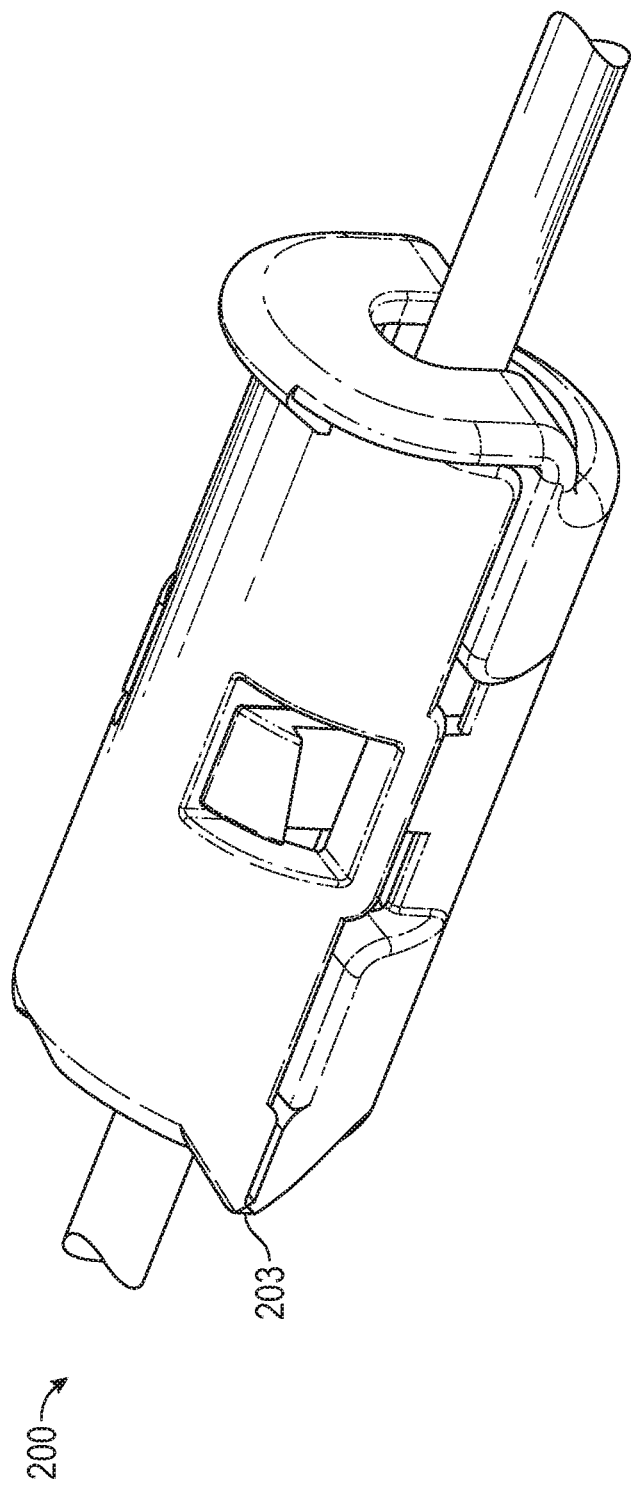
FIG. 2D illustrates the pinch clamp of FIG. 2A in an assembled, engaged position.
Figure 2E:
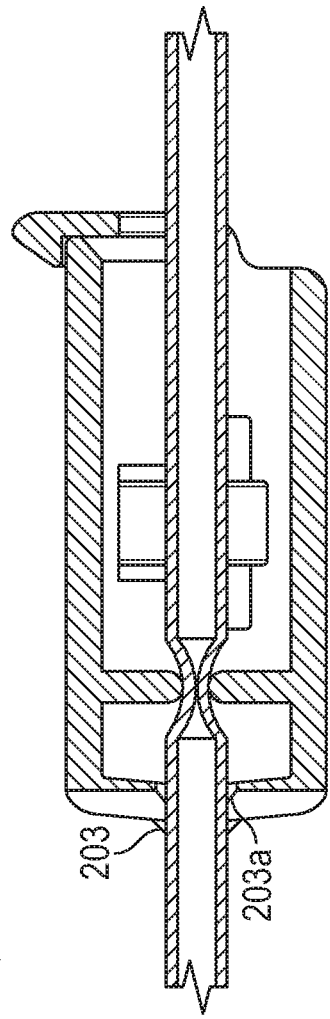
FIG. 2E illustrates a cross-sectional side view of the pinch clamp of FIG. 2A in the assembled, engaged position.

FIGS. 1A-1E illustrate a pinch clamp 100 that is configured in accordance with one or more embodiments of the present invention. In FIG. 1A, pinch clamp 100 is shown in a pre-assembled position. FIGS. 1B and 1C show pinch clamp 100 in an assembled, disengaged position, while FIGS. 1D and 1E show pinch clamp 100 in an assembled, engaged position. Pinch clamp 100 generally comprises a first arm 101 and a second arm 102 which are interconnected by living hinges 103. Living hinges 103 comprise thin flexible lengths of the same material from which first arm 101 and second arm 102 are made. In other words, pinch clamp 100 can be molded from a single material.

Living hinges 103 can be positioned on opposing sides of pinch clamp 100 to thereby form a hinge opening 103a between the living hinges. Hinge opening 103a can function as a passageway through which intravenous tubing 150 may extend through pinch clamp 100. Second arm 102 can include an end wall 107 having a wall opening 107a which forms an opposing passageway through which intravenous tubing 150 may also extend. Living hinges 103 allow first arm 101 to be positioned overtop second arm 102 into an assembled position and to be repeatedly engaged with second arm 102 as will be further described below. The length of living hinges 103 can be sufficient to cause them to take on a rounded shape when pinch clamp 100 is in the assembled position. In other words, living hinges 103 bend but do not fold.

First arm 101 and second arm 102 have a generally rounded shape such that, when assembled, pinch clamp 100 forms a cylindrical shape. First arm 101 and second arm 102 each include corresponding clamping surfaces 104a, 104b respectively which align when pinch clamp 100 is assembled as is shown in FIGS. 1C and 1E. First arm 101 further includes openings 105a, 105b on opposing sides of the arm. Openings 105a, 105b correspond to retaining tabs 106a, 106b which are formed on opposing sides of second arm 102. When assembled, retaining tabs 106a, 106b insert through openings 105a, 105b respectively to retain pinch clamp 100 in the assembled, disengaged position as is shown in FIGS. 1B and 1C. More specifically, retaining tabs 106a, 106b can include ledges 106a1, 106b1 respectively which catch on retaining surfaces 105a1, 105b1 of openings 105a, 105b respectively to prevent first arm 101 from separating from second arm 102.

When in the assembled, disengaged position, clamping surfaces 104a, 104b do not occlude tubing 150 as is shown in FIG. 1C. To orient pinch clamp 100 in the engaged position, first arm 101 can be forced towards second arm 102 until engaging surface 108a which is formed on a terminal end of first arm 101 is positioned underneath engaging ledge 108b that extends inwardly from end wall 107 as is shown in FIG. 1E. In this engaged position, clamping surfaces 104a, 104b occlude tubing 150 to thereby restrict fluid flow.

One disadvantage of many prior art pinch clamps is that it is possible to disengage the pinch clamp by applying a lateral force between the first and second arms. With reference to FIG. 1E, this lateral force would be in a direction into or out from the figure. In essence, such a lateral force could cause the first arm to move sideways with respect to the second arm to the point that the first arm is freed from the second arm.

Pinch clamp 100 is designed to minimize the likelihood of this type of lateral disengagement. In particular, in addition to retaining pinch clamp 100 in an assembled position, retaining tabs 106a, 106b also limit lateral displacement of first arm 101. As shown in FIG. 1D, in the engaged position, retaining tabs 106a, 106b are positioned immediately inside the sidewalls of first arm 101. If a lateral force is applied between first arm 101 and second arm 102, retaining tabs 106a, 106b will contact first arm 101 to limit the lateral movement of first arm 101 relative to second arm 102. As a result, engaging surface 108a cannot be freed from engaging ledge 108b by laterally displacing first arm 101—at least without a significant, intentional force that would break or otherwise damage retaining tabs 106a, 106b. In some embodiments, such as is depicted in FIGS. 1A-1E, first arm 101 may include an extended portion 101a positioned below openings 105a, 105b which causes the point of contact between retaining tabs 106a, 106b and first arm 101 to be near the base of the retaining tabs. By positioning the point of contact near the base, retaining tabs 106a, 106b will be less likely to bend in response to a lateral force. The design of pinch clamp 100 therefore ensures that the clamp will only be disengaged intentionally by applying a force to pivot end wall 107 away from first arm 101.

Another advantage of the design of pinch clamp 100 is that it allows the pinch clamp to be molded with a two piece mold. As represented in FIG. 1A, pinch clamp 100 can be manufactured in the flat position and then assembled into the position shown in FIG. 1B. As those of skill in the art will understand, because of this, and because of the configuration of each component, a two piece mold can be employed thereby simplifying the manufacturing process.

Additionally, as indicated above, pinch clamp 100 can have a generally cylindrical shape when assembled. This cylindrical shape lacks sharp edges which may enhance patient comfort as well as clinician comfort during use.

In some embodiments, pinch clamp 100 may alternatively be configured to include retaining tabs 106a, 106b on first arm 101 and openings 105a, 105b on second arm 102. In such cases, pinch clamp 100 can function in the same manner as described above. In some embodiments, a pinch clamp may be configured with a retaining tab and an opening on only one side of the arms as opposed to the opposing retaining tabs and openings that are depicted in the figures.

Also, many different types of clamping surfaces 104a, 104b may be employed in addition to those depicted in the figures. For example, the figures depict an instance where clamping surfaces 104a, 104b form clamping structures that are generally aligned and symmetrical. However, in some embodiments, clamping surfaces 104a, 104b can be configured to provide positive fluid displacement during the clamping process. In this context, positive displacement refers to causing fluid to flow in a direction towards end wall 107 (which is assumed to be towards the patient) as clamping surfaces 104a, 104b occlude tubing 150. To accomplish this positive displacement, clamping surface 104a, 104b can be shaped to cause tubing 150 to be progressively occluded in a direction towards end wall 107. For example, one or both of clamping surfaces 104a, 104b could comprise angled surfaces. Alternatively, one or both of clamping surfaces 104a, 104b may include multiple clamping structures. A number of suitable clamping surface configurations that can accomplish positive fluid displacement are disclosed in U.S. Provisional Patent Application Nos. 62/247, 615 filed on Oct. 28, 2015 and 62/296,372 filed on Feb. 17, 2016.

FIGS. 2A-2E illustrate another pinch clamp 200 that is configured in accordance with one or more embodiments of the present invention. Pinch clamp 200 is structured and functions in substantially the same manner as pinch clamp 100. However, pinch clamp 200 includes living hinges 203 which fold rather than bend. Living hinges 203 can comprise opposing short lengths of material which couple the first and second arms of pinch clamp 200 together and form a hinge opening 203a. This short length causes living hinges 203 to take on a folded shape when pinch clamp 200 is assembled.

Figure 3:
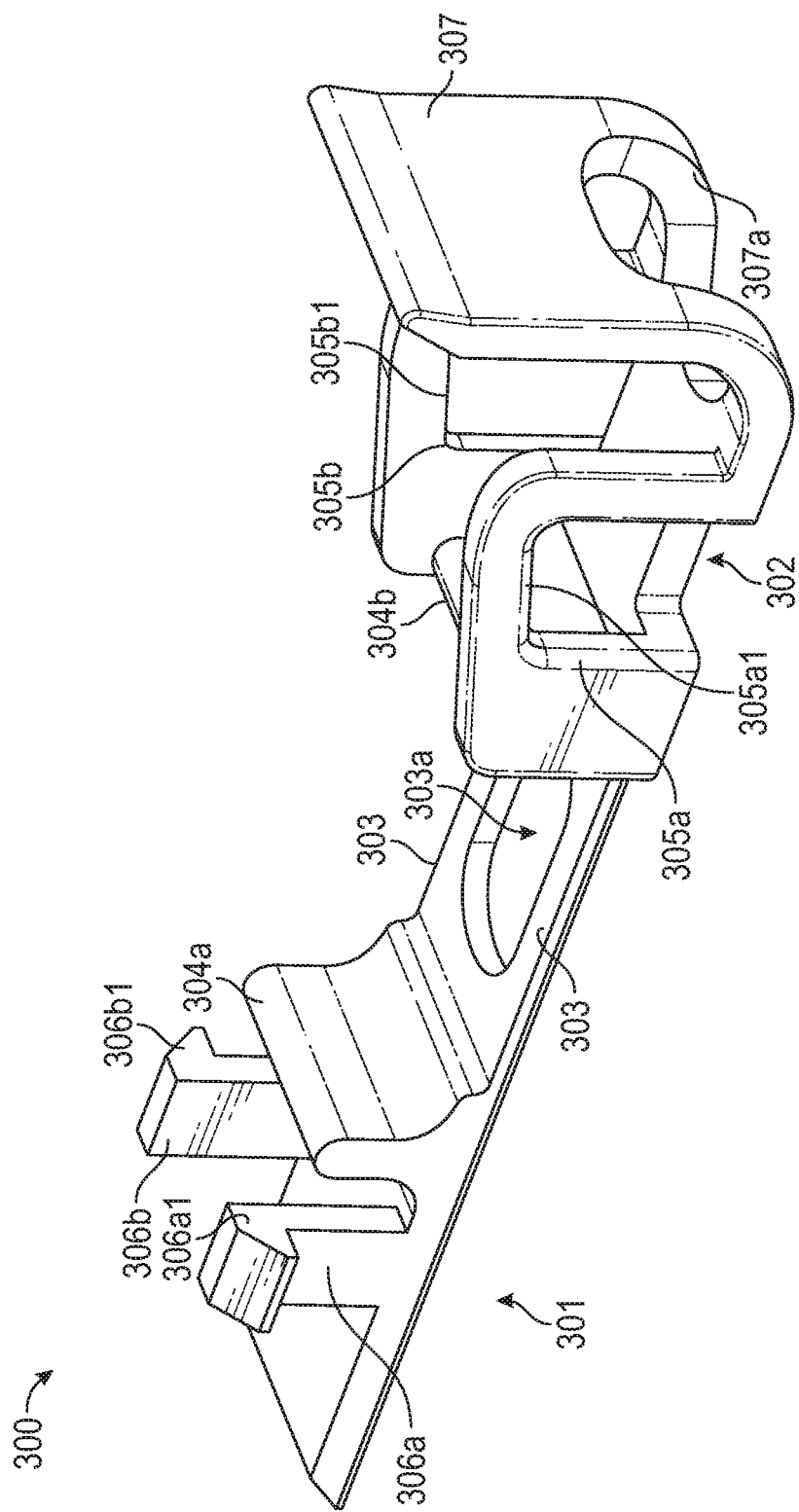
FIG. 3 illustrates a pinch clamp in accordance with one or more additional embodiments of the present invention in which the pinch clamp is oriented in a pre-assembled position.

FIG. 3 illustrates another pinch clamp 300 that is configured in accordance with one or more embodiments of the present invention. Pinch clamp 300 is similar to pinch clamp 100 except that pinch clamp 300 does not have a generally rounded shape. Accordingly, FIG. 3 includes reference numerals similar to those in FIG. 1 to identify the similar components. Most notably, pinch clamp 300 illustrates an embodiment where retaining tabs 306a, 306b are formed on first arm 301 while openings 305a, 305b are formed on second arm 302. In all regards, pinch clamp 300 can function in the same manner as described above.

Figure 4A:
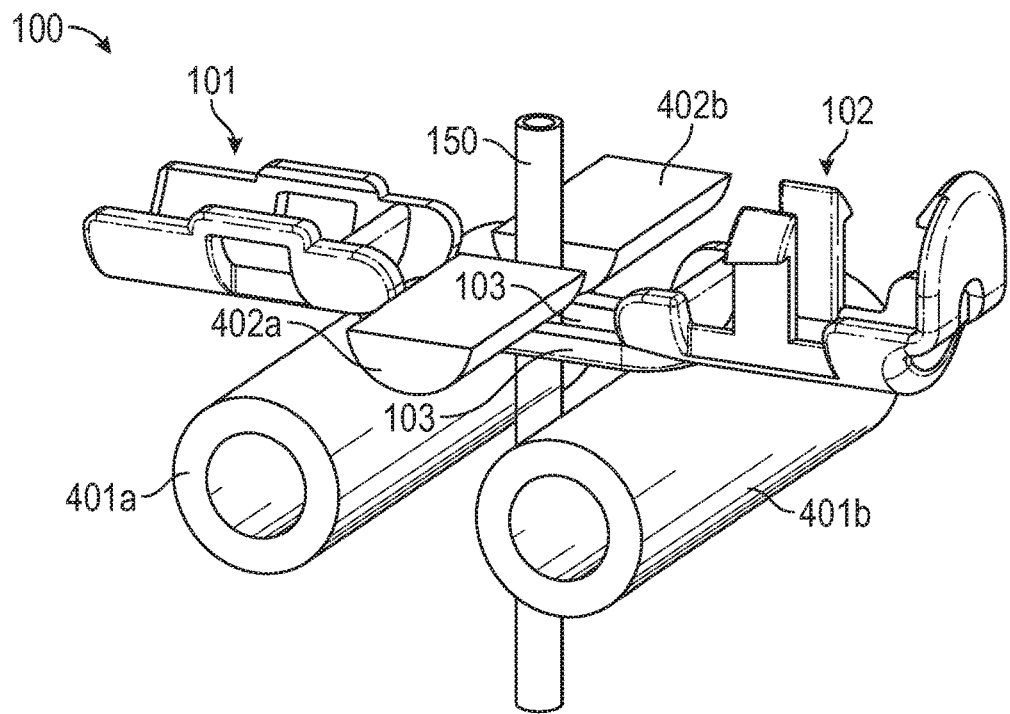
FIGS. 4A-4C illustrate an assembly sequence that can be performed to assemble the pinch clamps of the present invention.
Figure 4B:
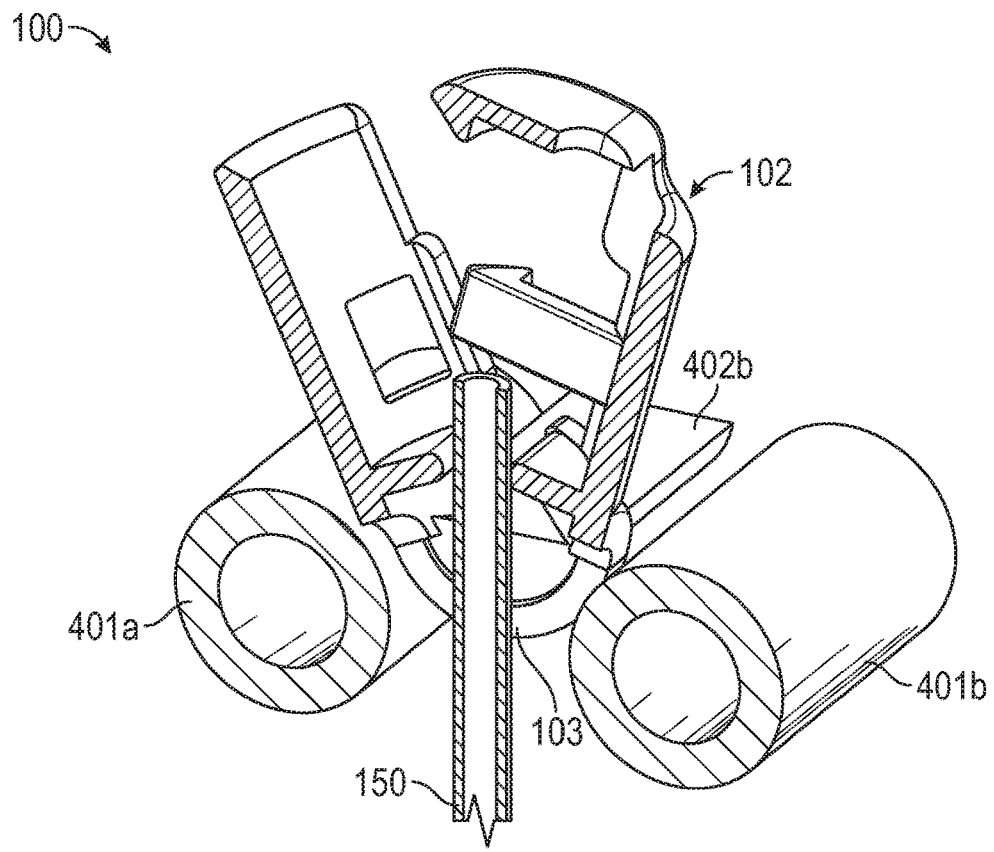
Figure 4C:
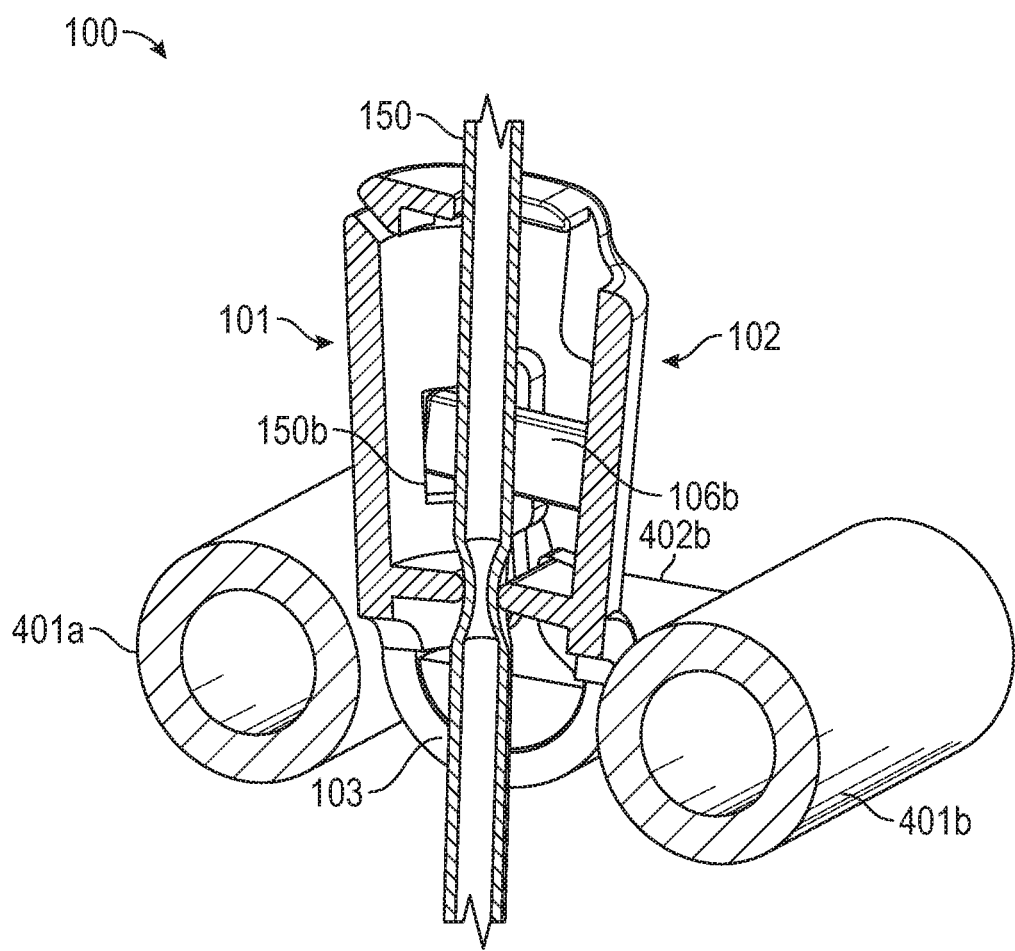

In addition to facilitating manufacturing, the flat, unassembled orientation of the pinch clamps of the present invention also facilitates assembly. FIGS. 4A-4C illustrate a sequence of steps that can be employed to assemble a pinch clamp into the assembled, disengaged position. Allow FIGS. 4A-4C depict this assembly process on pinch clamp 100, the same process could be employed to assemble pinch clamp 200 or pinch clamp 300.

Pinch clamp 100 may be formed and processed by any compatible means or methods of manufacturing. With reference to FIG. 4A, pinch clamp 100 is shown positioned atop two stationary rollers 401a, 401b in the flat, unassembled orientation with retaining tabs 106a, 106b pointing upwards. In some instances, pinch clamp 100 is alternatively positioned atop a slot formed by two stationary surfaces. In this orientation, two moveable pins 402a, 402b can be positioned atop living hinges 103, and tubing 150 can be inserted upwardly through hinge opening 103a. Then, as shown in FIG. 4B, which illustrates a cross-sectional view, pins 402a, 402b can be moved downwardly towards stationary rods 401a, 401b. This downward movement will cause living hinges 103 to flex inwardly thereby closing first arm 101 overtop second arm 102. FIG. 4C illustrates that this downward movement of pins 402a, 402b can continue to the point that ledges 106a1, 106b1 of retaining tabs 106a, 106b have bypassed retaining surfaces 105a1, 105b1 of openings 105a, 105b thereby interconnecting first arm 101 to second arm 102. Also, tubing 150 can be further inserted through hinge opening 103a and out through wall opening 107a to a desired distance. In some embodiments, such as is shown in FIG. 4C, a spacing between clamping surfaces 104a, 104b can be small enough that tubing 150 is slightly secured, but not occluded, when pinch clamp 100 is in the assembled, disengaged position to thereby prevent pinch clamp 100 from sliding along tubing 150. Once first arm 101 has been interconnected with second arm 102, pins 402a, 402b can be withdrawn thus completing the assembly process.

Figure 5A:
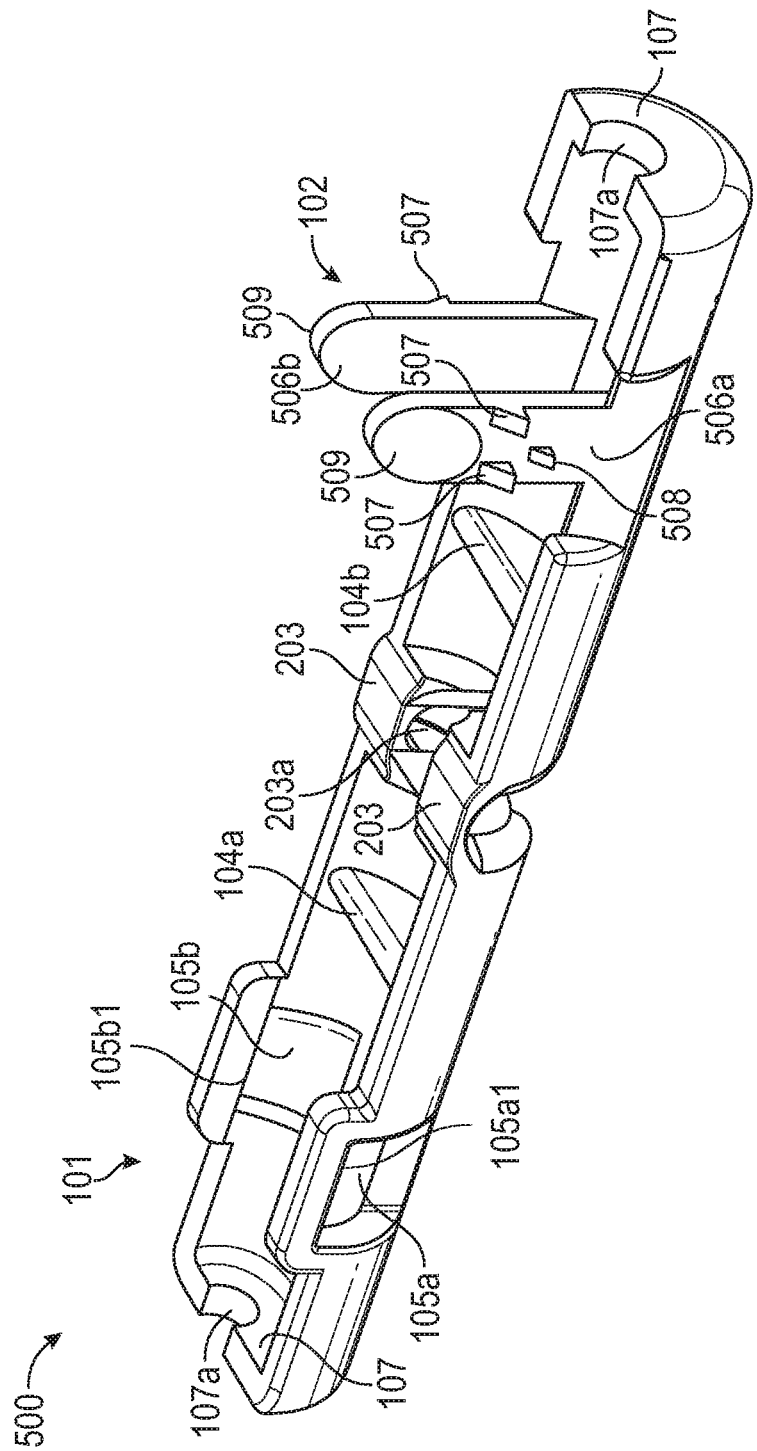
FIGS. 5A-5C illustrates a pinch clamp in accordance with one or more additional embodiments of the present invention in which the retaining tabs include separate pinch and clamp surfaces.
Figure 5B:
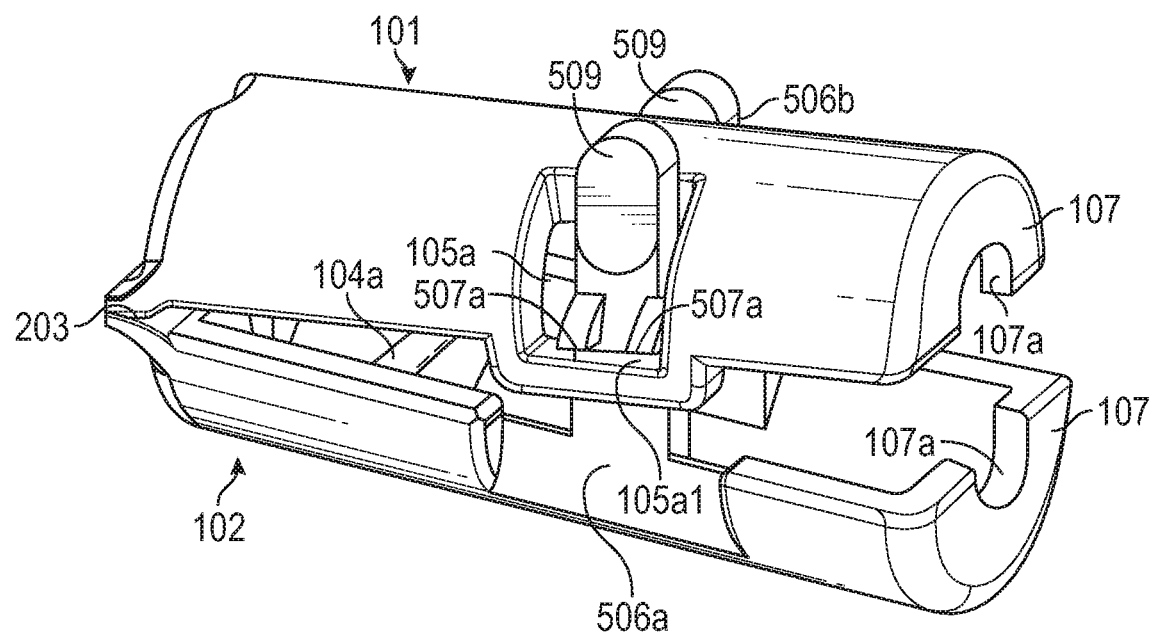
Figure 5C:
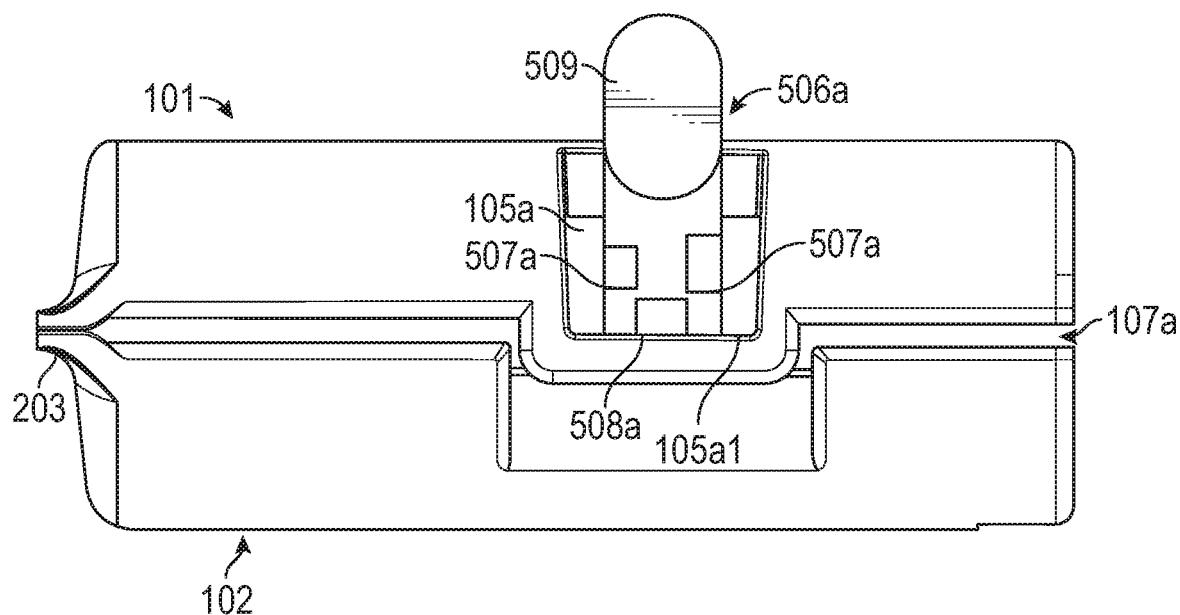

FIGS. 5A-5C illustrate another pinch clamp 500 that is configured in accordance with one or more embodiments of the present invention. FIGS. 5A-5C depict pinch clamp 500 in an unassembled position, an assembled, disengaged position, and an engaged position respectively. Pinch clamp 500 has many similar components as pinch clamps 100 and 200 which are identified with similar references. Unlike pinch clamps 100, 200, pinch clamp 500 includes tabs 506a, 506b in place of retaining tabs 106a, 106b. Also, in pinch clamp 500, end wall 107 is split between first arm 101 and second arm 102 and does not include engaging ledge 108b for reasons that will become apparent below.

Tabs 506a, 506b can each include one or more retaining protrusions 507 (of which two are shown in the figures) and a clamping protrusion 508. Retaining protrusions 507 can form retaining ledges 507a that can serve a similar purpose as ledges 106a1, 106a2 described above, namely, retaining pinch clamp 500 in the assembled position. Clamping protrusions 508 can also form clamping ledges 508a that function to secure pinch clamp 500 in the engaged position and therefore replace engaging ledge 108b for this purpose.

Both retaining ledges 507a and clamping ledges 508a can be configured to interface with retaining surfaces 105a1, 105b1. For example, in FIG. 5B, first arm 101 has been folded overtop second arm 102 to the point that tabs 106a, 106b have inserted through openings 106a, 106b until retaining ledges 507a abut retaining surfaces 105a1, 105b1. Tabs 506a, 506b can be biased outwardly so that first arm 101 will remain in this assembled, disengaged position absent an outside force. The sloped upper surface of retaining protrusions 507 can also facilitate sliding first arm 101 into this position.

FIG. 5C illustrates how pinch clamp 500 can be moved into the engaged position. In particular, as first arm 101 is forced towards second arm 102, clamping ledges 508a will come clear of retaining surfaces 105a1, 105b1 thereby causing tabs 105a, 105b to pivot slightly outward. At this point, clamping ledges 508a will contact retaining surfaces 105a1, 105b1 to retain pinch clamp 500 in the engaged position. For this reason, there is no need for engaging ledge 108b on end wall 107 thereby allowing end wall 107 to be split between the two arms as shown. One benefit of splitting end wall 107 and therefore splitting wall opening 107a is that intravenous tubing 150 will not need to be threaded through wall opening 107a during assembly.

To ensure that clamping protrusions 508 will not prevent retaining protrusions 507 from engaging with retaining surfaces 105a1, 105b1, retaining protrusions 507 can extend outwardly farther than clamping protrusions. In particular, clamping protrusion 508 will typically be positioned directly within the structure of first arm 101 that forms opening 105a, 105b and may therefore cause tab 506a, 506b to be pivoted slightly inwardly. To ensure that this slightly inward pivoting does not cause pinch clamp 500 to become disassembled, retaining protrusions 507 can extend outwardly sufficiently to remain in contact with retaining surfaces 105a1, 105b1 even while clamping protrusions 508 force tabs 506a, 506b inwardly.

To facilitate transitioning pinch clamp 500 from the engaged position to the disengaged position or from the disengaged position to the disassembled position, tabs 506a, 506b can include a squeezing surface 509 positioned above retaining protrusions 507. Squeezing surface 509 can generally be configured as a relatively flat extension of tab 506a, 506b that is sized to accommodate a finger and thumb of the clinician. When an inward (or squeezing) force is applied to squeezing surfaces 509, tabs 506a, 506b will pivot inwardly to allow retaining surfaces 105a1, 105b1 to pass by clamping ledges 508a and/or retaining ledges 507a. In this way, pinch clamp 500 can be more easily manipulated.

Figure 6A:
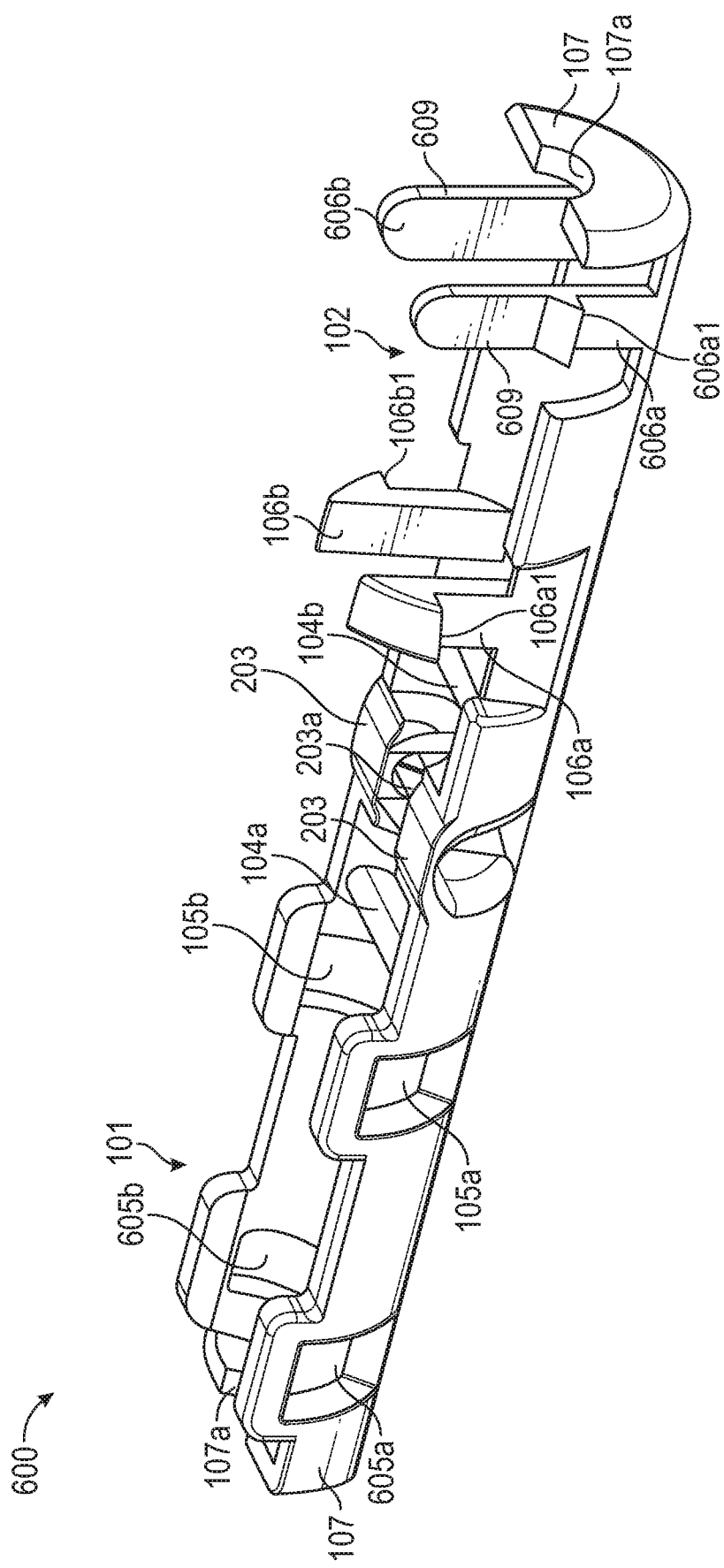
FIGS. 6A-6C illustrates a pinch clamp in accordance with one or more additional embodiments of the present invention in which the pinch clamp includes pinch tabs that are separate from the retaining tabs.
Figure 6B:
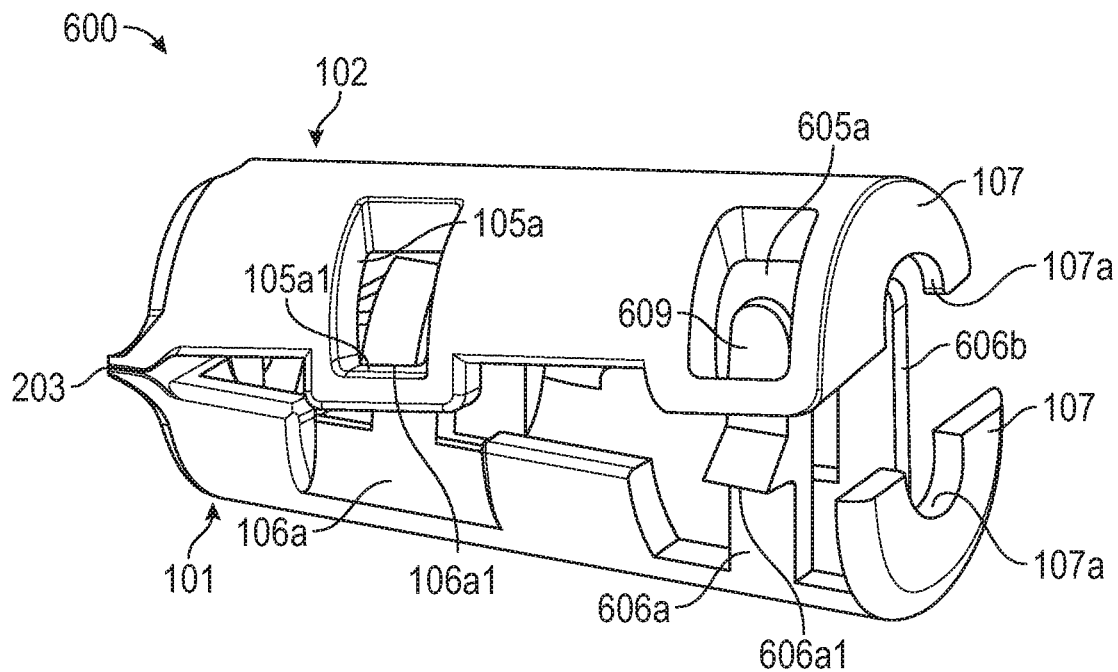
Figure 6C:
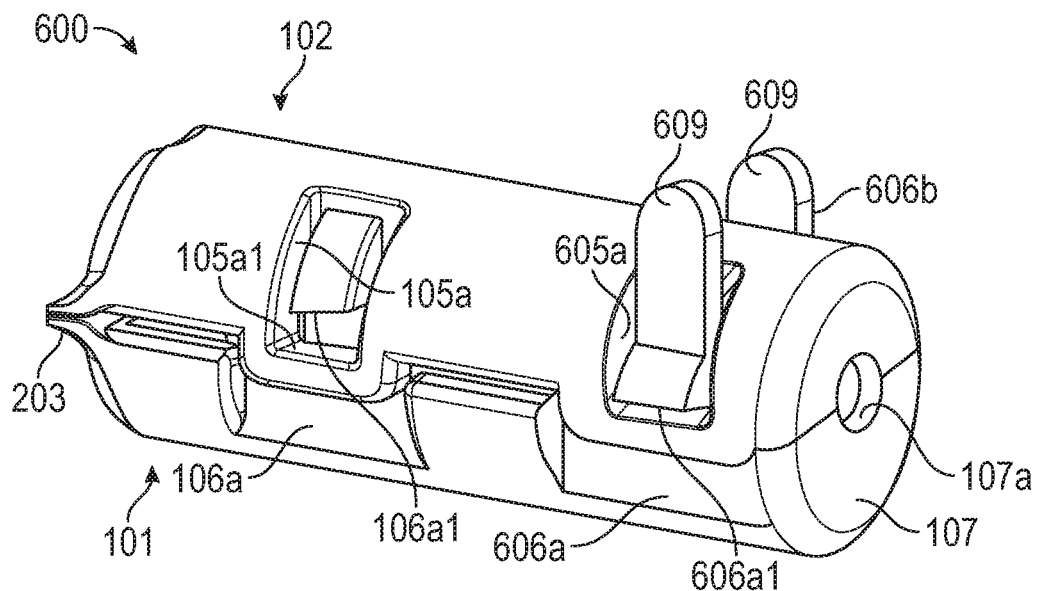
Figure 7A:
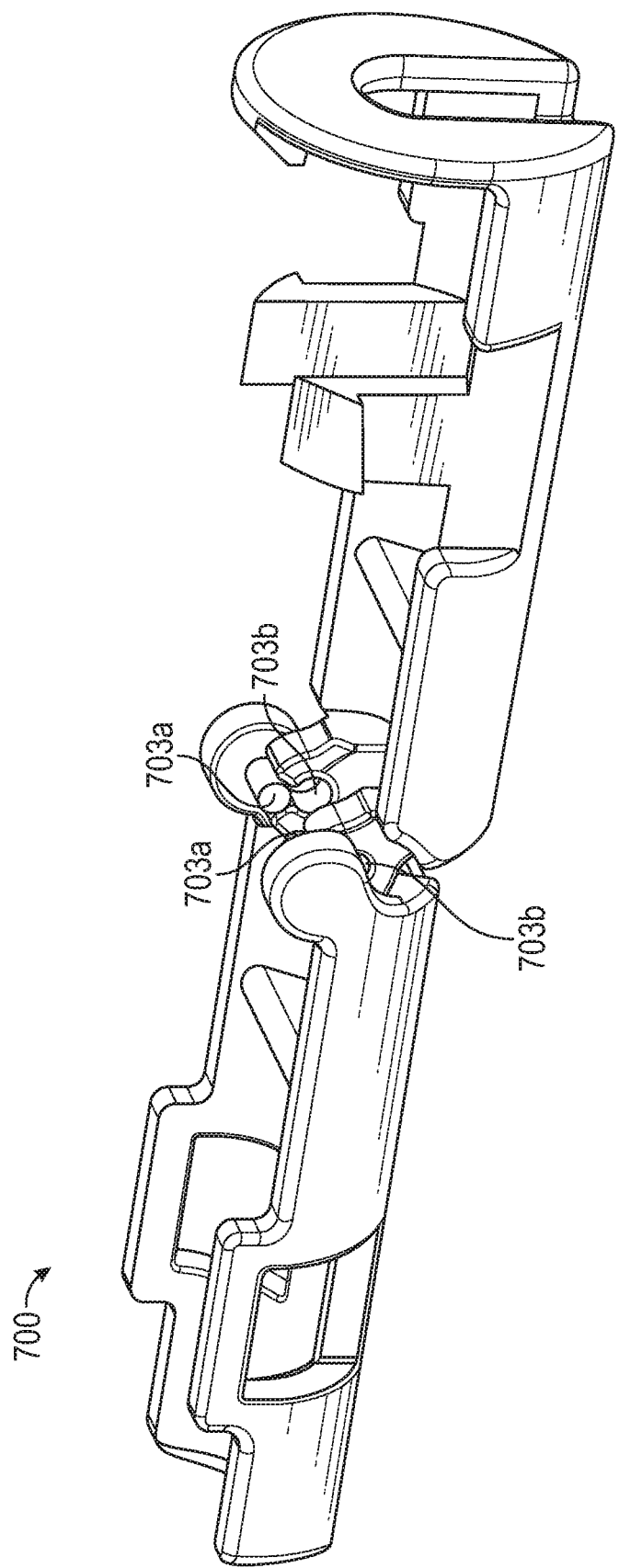
FIGS. 7A-7E illustrate a pinch clamp in accordance with one or more additional embodiments of the present invention in which the pinch clamp includes a separable hinge.
Figure 7B:
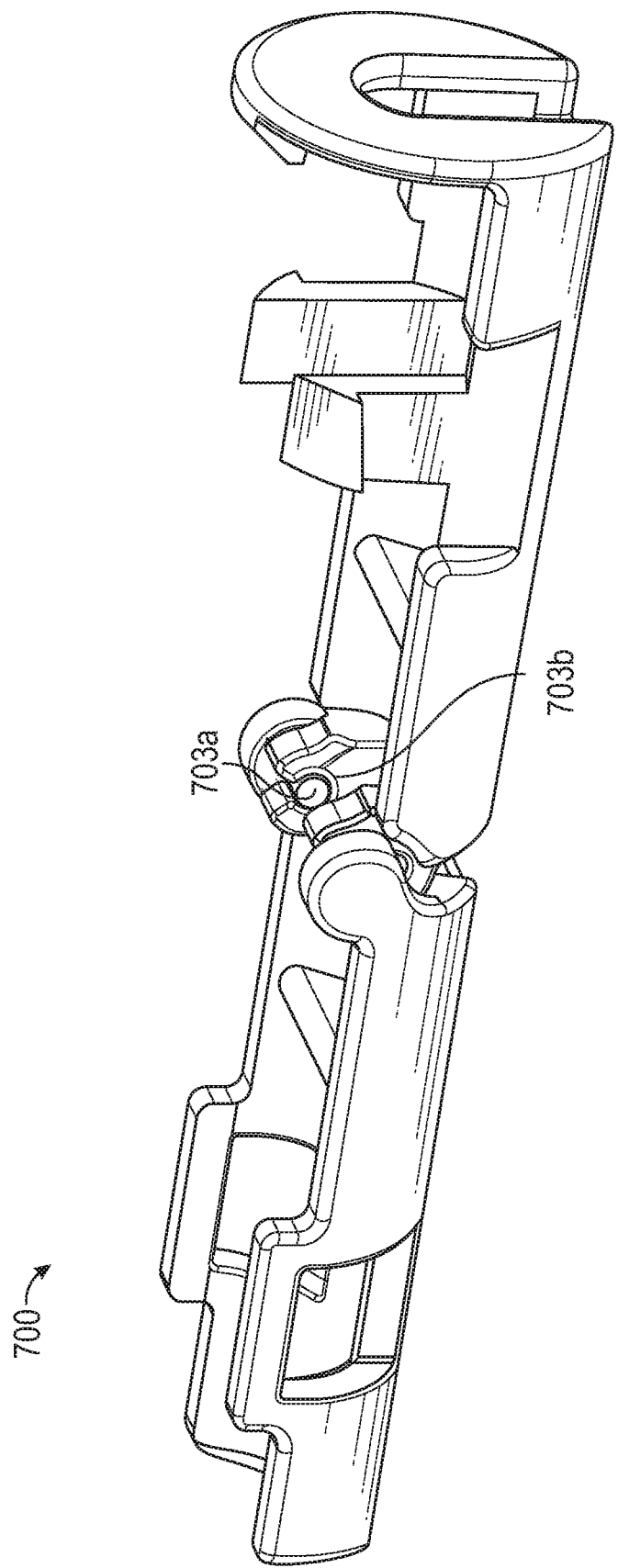
Figure 7C:
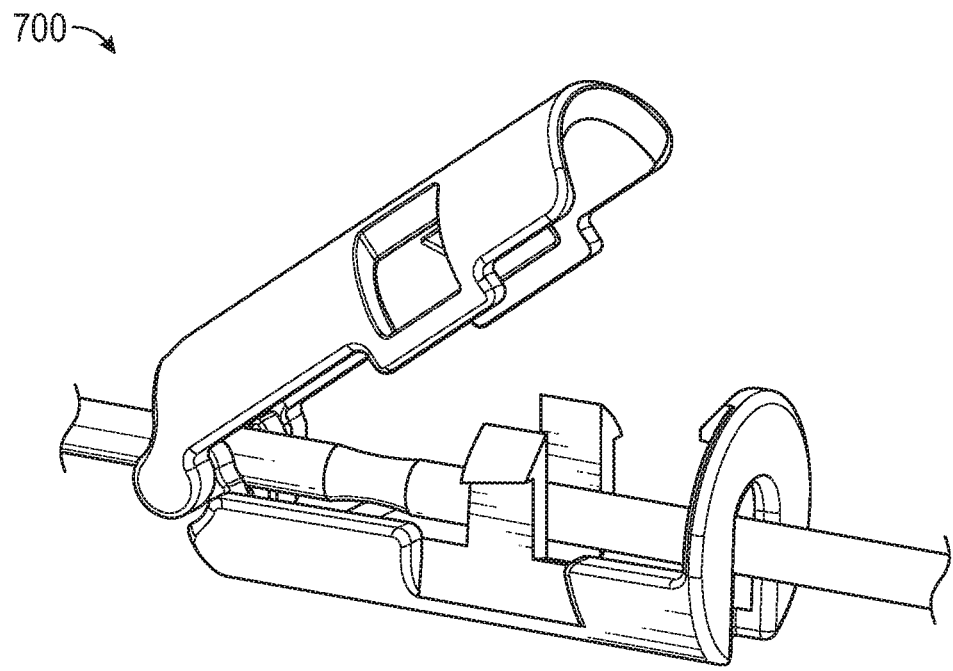
Figure 7D:
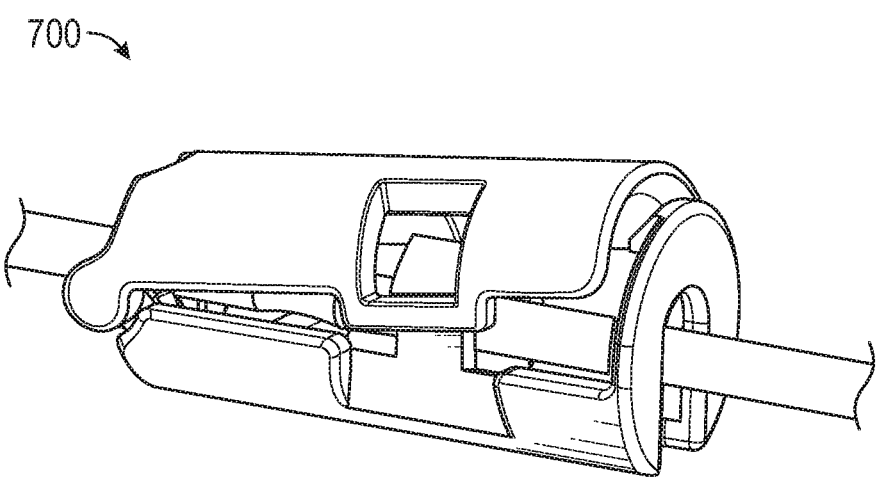
Figure 7E:
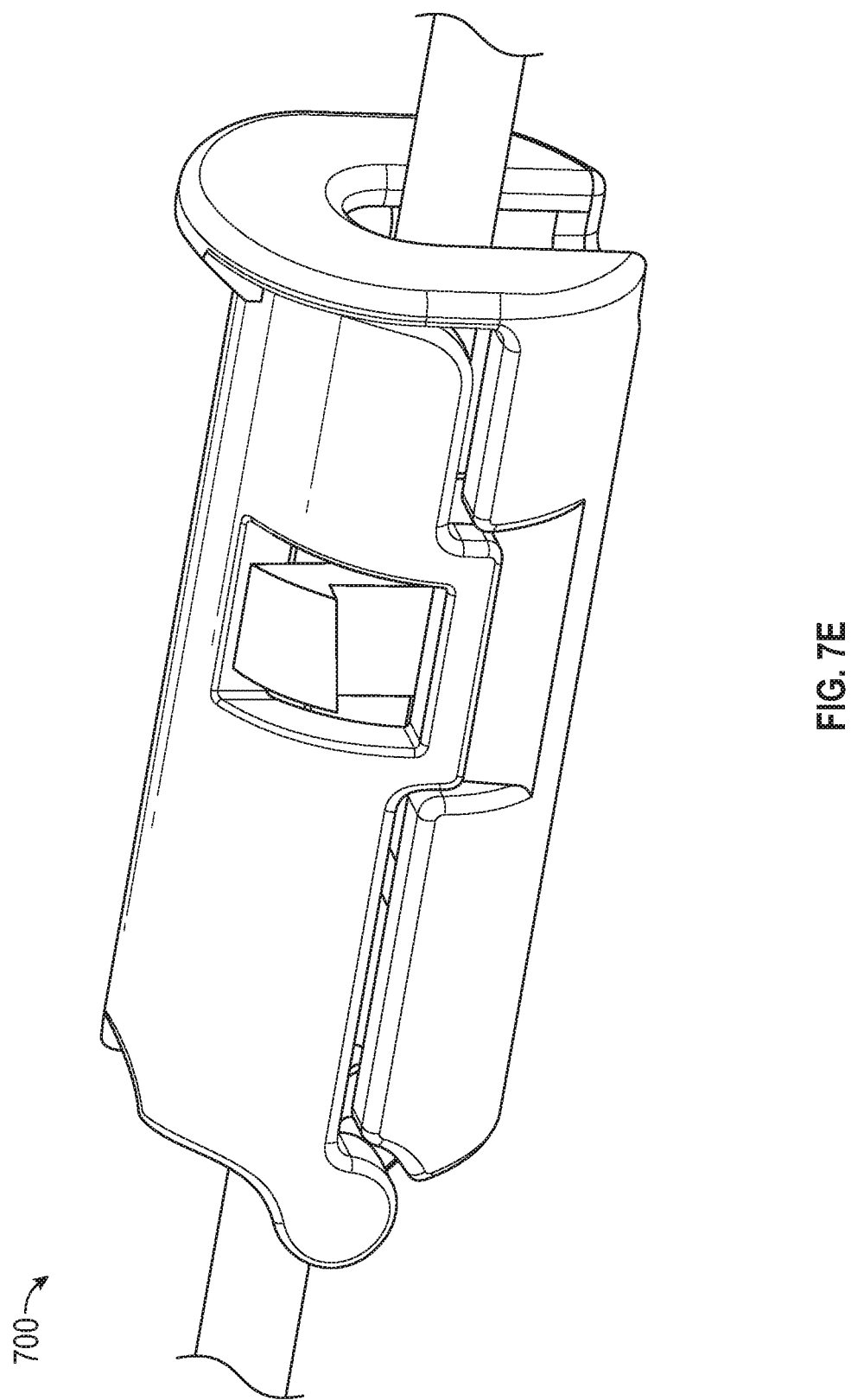

FIGS. 6A-6C illustrate another pinch clamp 600 that is configured in accordance with one or more embodiments of the present invention. FIGS. 6A-6C depict pinch clamp 600 in an unassembled position, an assembled, disengaged position, and an engaged position respectively. Pinch clamp 600 also has many similar components as pinch clamps 100 and 200 which are identified with similar references.

As with pinch clamps 100 and 200, pinch clamp 600 also includes openings 105a, 105b and retaining tabs 106a, 106b which provide the same function of retaining pinch clamp 600 in the assembled position. In contrast, to pinch clamps 100 and 200 however, pinch clamp 600 includes separate clamping openings 605a, 605b and clamping tabs 606a, 606b. Clamping tabs 606a, 606b form clamping ledges 606a1, 606b1 respectively which serve a similar function as clamping ledges 508a.

FIG. 6B illustrates how pinch clamp 600 can be retained in the assembled position due to the interface between ledges 106a1, 106b1 and retaining surfaces 105a1, 105b1 in the same manner as described above. When in this assembled position, clamping ledges 606a1, 606b1 will be positioned below clamping surfaces 605a1, 605b1 respectively. Then, as first arm 101 is pressed towards second arm 102, clamping tabs 606a, 606b will pivot inwardly to allow clamping ledges 606a1, 606b1 to slide overtop clamping surfaces 605a1, 605b1. Clamping tabs 606a, 606b can be outwardly biased so that clamping ledges 606a1, 606b1 will remain overtop clamping surfaces 605a1, 605b1 to thereby secure pinch clamp in the engaged position.

Because clamping tabs 606a, 606b retain pinch clamp 600 in the engaged position, there is no need to form engaging ledge 108b on end wall 107. Accordingly, end wall 107 can be split between the two arms as described above. Also, clamping tabs 606a, 606b can include squeezing surfaces 609 to facilitate pivoting clamping tabs 606a, 606b inwardly to transition pinch clamp 600 from the engaged position to the disengaged position.

FIGS. 7A-7E illustrate another pinch clamp 700 that is configured in accordance with one or more embodiments of the present invention. FIGS. 7A-7E illustrate pinch clamp 700 in a separated position, a separated, disassembled position, an assembled, disengaged position, and an engaged position respectively. Pinch clamp 700 is similar to pinch clamps 100 and 200 except that it employs a separable hinge. This separable hinge can be formed of opposing hinge pins 703a and corresponding hinge knuckles 703b. The length of hinge pins 703a can be truncated so as to not block the opening through which the intravenous tubing will pass. Hinge knuckles 703b can include a cutout (i.e., they can have a c-shape) which allows first arm 101 to be coupled to second arm 102 by pressing hinge pins 703a into hinge knuckles 703b.

In the depicted embodiment, hinge pins 703a are oriented inwardly. However, in other embodiments, hinge pins 703a can be oriented outwardly. One way in which this can be accomplished is by forming hinge pins 703a and hinge knuckles 703b on the opposite arms from what is shown in FIGS. 7A-7E.

A primary benefit of employing a separable hinge is that pinch clamp 700 can be assembled by threading the tubing through the wall opening prior to coupling the two arms together. Then, with the tubing threaded, the other arm can be coupled and rotated into the assembled position. Although pinch clamp 700 is shown as having an end wall similar to the end wall in pinch clamps 100 and 200, pinch clamp 700 could alternatively be configured to include the features of pinch clamp 500 or pinch clamp 600 so that the end wall could be split between the two arms. This would allow pinch clamp 700 to be assembled without threading the tubing through any opening.

Figure 8A:
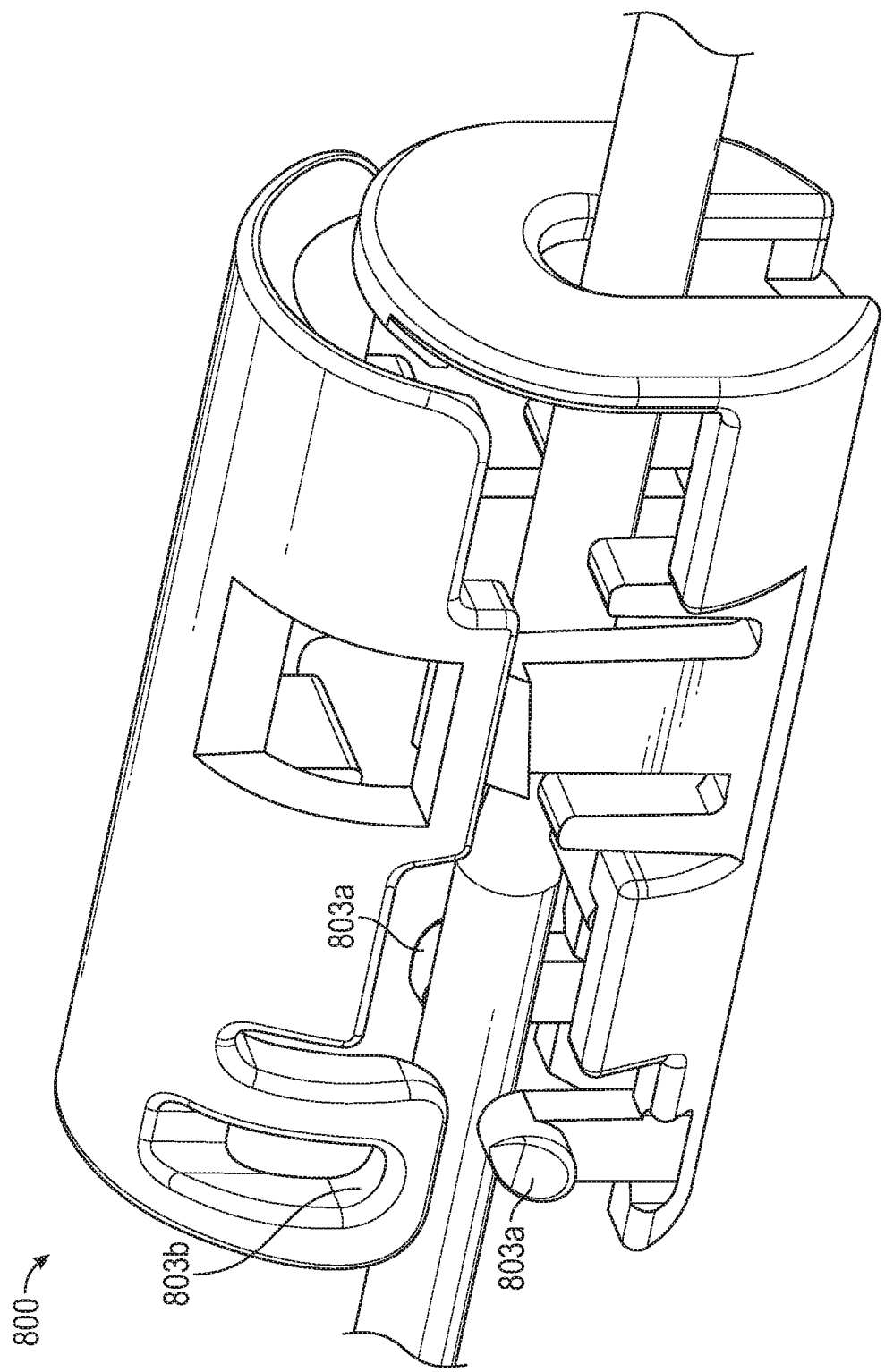
Figure 8C:
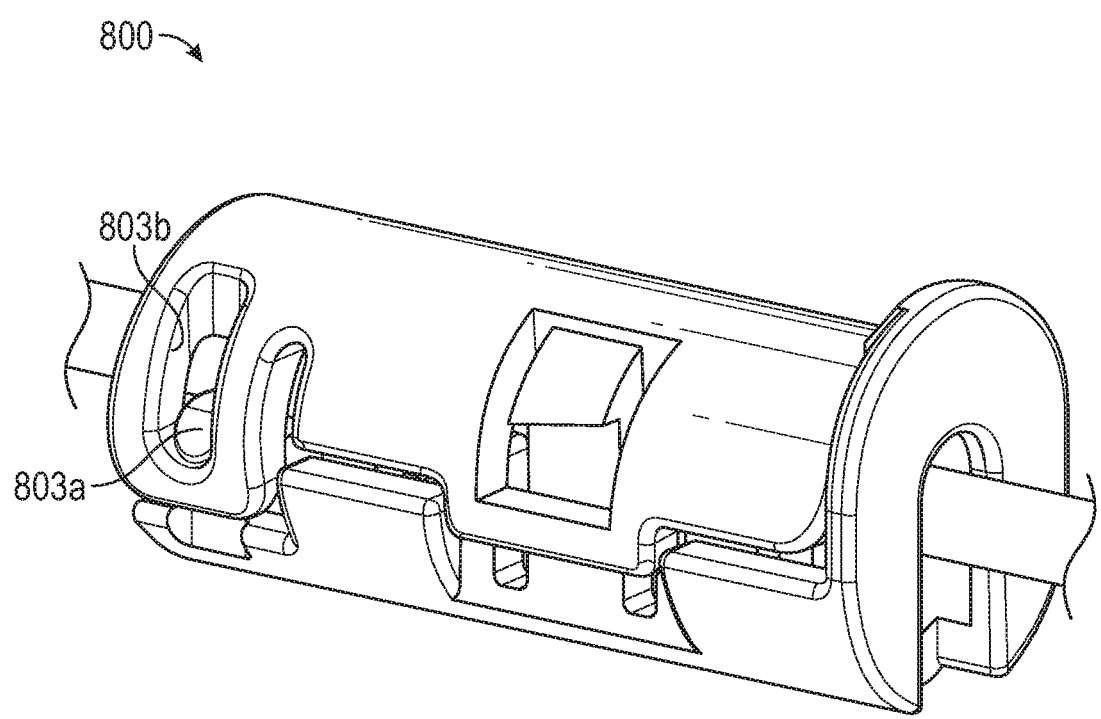

FIGS. 8A-8C illustrate another pinch clamp 800 that is configured in accordance with one or more embodiments of the present invention. FIGS. 8A-8C illustrate pinch clamp 800 in a separated position, an assembled, disengaged position, and an engaged position respectively. Like pinch clamp 700, pinch clamp 800 includes a separable hinge. However, the separable hinge of pinch clamp 800 is configured to allow the pinch clamp to be assembled in a linear fashion (i.e., without having to couple the arms when they are positioned in a row and then rotate one arm 180° to the assembled position).

The separable hinge of pinch clamp 800 is formed of opposing hinge pins 803a which are oriented outwardly on one arm and hinge knuckles 803b which are configured as elongated openings on the other arm. To assemble pinch clamp 800, the two arms can be placed on top of one another and hinge pins 803a can be forced into hinge knuckles 803b by squeezing the two arms together (i.e., using a linear force). Because hinge knuckles 803b are formed as openings within the body of the arm itself, the arm can flex sufficiently outward to allow the two arms to be snapped together with this linear force. In other words, the same squeezing force can accomplish both the coupling of the hinge and the assembly of the pinch clamp into the disengaged position.

As with pinch clamp 700, a primary benefit of the separable hinge of pinch clamp 800 is that the intravenous tubing can be threaded through the wall opening without having to first couple the two arms together and therefore without having to thread the tubing through the hinge opening. Also, pinch clamp 800 could be configured with the features of pinch clamp 500 or 600 so that there would be no need to thread the tubing through the wall opening. In such cases, the tubing could be placed on top of one arm and then the other arm could be placed on top and squeezed together to assemble the pinch clamp.

Any of the various embodiments of pinch clamps described herein can be configured to include clamping surfaces that provide positive displacement of fluid when the tubing is clamped. FIGS. 9A and 9B provide an example of how clamping surfaces 104a, 104b could be configured to provide this positive displacement. As shown, clamping surfaces 104a, 104b include a proximal bump 104a1, 104b1 that protrudes from a distal surface 104a2, 104b2 respectively. In this context, distal refers to the end of the pinch clamp that will be oriented closer to the patient.

Due to this configuration, proximal bumps 104a1, 104b1 will occlude the tubing first during the engagement motion. Then, as distal surfaces 104a2, 104b2 come closer together, they will compress a downstream section of the tubing thereby forcing fluid (e.g., saline) contained therein to be forced distally. This distal flow of fluid will in turn cause blood that may have entered the downstream catheter to be flushed into the patient's vasculature. It is believed that this type of flushing will increase the safe dwell time of the catheter.

Although the generally rounded shape of the pinch clamps of some embodiments of the present invention can enhance patient comfort, it can also increase the difficultly of engaging and disengaging the clamp. For this reason, in some embodiments, a pinch clamp can include one or more textured surfaces to enhance a clinician's grip on the pinch clamp. For example, with reference to FIGS. 1B and 2B, a top surface of first arm 101 and a bottom surface of second arm 102 can include a texture to prevent a clinician's fingers from slipping when attempting to engage the pinch clamp. In some embodiments, this texture could be located towards end wall 107. Also, in some embodiments, this texture can be provided in the form of a soft material that differs from the material from which the remainder of the pinch clamp is formed. Examples of suitable textures, soft materials, and their placement are described in U.S. Provisional Patent Application Nos. 62/247,615 filed on Oct. 28, 2015 which is incorporated herein by reference. As a specific example and with reference to the design of pinch clamp 100, a soft material may be employed along a top, inner surface of end wall 107 against which the clinician may press to disengage the pinch clamp.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A pinch clamp comprising:
a first arm coupled to a second arm by a hinge;
wherein the first arm includes a first clamping surface and the second arm includes a second clamping surface;
wherein one of the first arm or the second arm includes an opening and the other of the first arm or the second arm includes a retaining tab which inserts through the opening when the first arm is positioned overtop the second arm, the retaining tab interfacing with the opening to prevent the first arm from separating from the second arm,
wherein the retaining tab includes a retaining ledge that interfaces with the opening to prevent the first arm from separating from the second arm, wherein the retaining tab further includes a clamping ledge that interfaces with the opening to retain the pinch clamp in an engaged position.

2. The pinch clamp of claim 1, wherein the retaining ledge extends outwardly through the opening such that the retaining tab provides reinforcement against lateral displacement of the first arm.

3. The pinch clamp of claim 1, wherein the retaining tab includes a squeezing surface.

4. The pinch clamp of claim 1, wherein the first and second clamping surfaces are configured to clamp tubing in a manner that causes positive fluid displacement.

5. The pinch clamp of claim 4, wherein the first clamping surface is angled.

6. The pinch clamp of claim 1, wherein the hinge bends to form a rounded shape when the first arm is positioned overtop the second arm.

7. The pinch clamp of claim 1, wherein the hinge folds on top of themselves when the first arm is positioned overtop the second arm.

8. The pinch clamp of claim 1, wherein the hinge is separable.

9. The pinch clamp of claim 1, wherein one or both of the first or second arms includes texture or a soft material on one or more outer surfaces.

10. A pinch clamp, comprising:
a first arm coupled to a second arm by a hinge,
wherein the first arm comprises a first clamping surface, a retaining surface, and another retaining surface on an opposite side of the first arm as the retaining surface;
wherein the second arm comprises a second clamping surface, a retaining tab, and another retaining tab on an opposite side of the second arm as the retaining tab, wherein the retaining tab comprises a ledge, wherein the other retaining tab comprises another ledge extending in an opposite direction as the ledge,
wherein the pinch clamp is configured to move from a disengaged position to an engaged position, wherein in the disengaged position, the retaining tab and the other retaining tab are biased outwardly such that the retaining tab abuts the retaining surface and the other retaining tab abuts the other retaining surface, wherein in the engaged position, the retaining tab is spaced apart from the retaining surface and the other retaining tab is spaced part from the other retaining surface.

11. The pinch clamp of claim 10, further comprising a tubing extending therethrough, wherein when the pinch clamp is in the engaged position, the first clamping surface and the second clamping surface occlude the tubing.

12. The pinch clamp of claim 10, wherein the ledge is lateral to a portion of the retaining tab and the other ledge is lateral to a portion of the other retaining tab.

13. The pinch clamp of claim 10, wherein the hinge is a living hinge.

14. The pinch clamp of claim 10, wherein the hinge comprises opposing hinge pins extending from the first arm or the second arm, wherein the hinge further comprises opposing hinge knuckles disposed within the first arm or the second arm, wherein the opposing hinge pins are configured to snap into the opposing hinge knuckles.

15. A pinch clamp comprising:
a first arm coupled to a second arm by a hinge;
wherein the first arm includes a first clamping surface and the second arm includes a second clamping surface;
wherein the second arm comprises a clamping tab and another clamping tab on an opposite side of the second arm as the clamping tab, wherein the clamping tab comprises a clamping ledge, wherein the other clamping tab comprises another clamping ledge extending in an opposite direction as the clamping ledge, wherein the first arm comprises a third clamping surface and a fourth clamping surface, wherein the clamping tab and the other clamping tab are configured to pivot inwardly to slide overtop the third clamping surface and the fourth clamping surface, respectively, wherein the first arm further comprises a first clamping opening proximate the third clamping surface and configured to receive the first clamping tab, wherein the first arm further comprises a second clamping opening proximate the fourth clamping surface, opposite the first clamping opening, and configured to receive the other clamping tab, wherein the first clamping opening and the second clamping opening are each enclosed and separate.

* * * * *